(12) United States Patent
Rajamani et al.

(10) Patent No.: US 8,314,209 B2
(45) Date of Patent: Nov. 20, 2012

(54) LIPID-ASSISTED SYNTHESIS OF POLYMER COMPOUNDS AND METHODS FOR THEIR USE

(75) Inventors: Sudha Rajamani, Cambridge, MA (US); Felix Olasagasti, Santa Cruz, CA (US); David W. Deamer, Santa Cruz, CA (US); Seico Benner, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 628 days.

(21) Appl. No.: 12/316,515

(22) Filed: Dec. 12, 2008

(65) Prior Publication Data
US 2009/0264621 A1   Oct. 22, 2009

Related U.S. Application Data

(60) Provisional application No. 61/007,575, filed on Dec. 12, 2007.

(51) Int. Cl.
*C07H 1/00* (2006.01)
*C07H 21/00* (2006.01)
*C07K 1/02* (2006.01)

(52) U.S. Cl. .................. 530/338; 536/25.3; 536/126

(58) Field of Classification Search .................. None
See application file for complete search history.

(56) References Cited

U.S. PATENT DOCUMENTS
7,772,390 B1 *   8/2010   Deamer ............... 536/25.3

OTHER PUBLICATIONS

D. Usher. Early Chemical Evolution of Nucleic Acids: a Theoretical Model. Science. Apr. 15, 1977, vol. 196, pp. 311-313.*
Lutay et al. The nonenzymatic template-directed ligation of oligonucleotides. Biogeosciences. 2006, vol. 3, pp. 243-249.*

* cited by examiner

*Primary Examiner* — Jeffrey E Russel
(74) *Attorney, Agent, or Firm* — Matthew Kaser; Adam Warwick Bell

(57) ABSTRACT

The invention herein disclosed provides for methods for the synthesis of polymers from monomers. In particular the method provides for the synthesis of polynucleotides from mononucleotides in the absence of catalytic enzymes. The method comprises providing an aqueous solution having a plurality of phospholipid molecules and monomer molecules; subjecting the aqueous solution to fluctuating temperature conditions; subjecting the aqueous solution to fluctuating cycles of drying and hydrating conditions; subjecting the aqueous solution to fluctuating $[H^+]$ conditions; the fluctuating conditions thereby allowing formation of a chemical bond between at least two monomers to create a polymer. The invention is of particular use in the fields of molecular biology, structural biology, cell biology, molecular switches, molecular circuits, and molecular computational devices, and the manufacture thereof.

25 Claims, 12 Drawing Sheets a)

b)

c)

LIPID-ASSISTED SYNTHESIS OF POLYMER COMPOUNDS AND METHODS FOR THEIR USE

The present application claims priority to and benefits of the following: U.S. Provisional Patent Application Ser. No. 61/007,575 entitled "Lipid-Assisted Synthesis Of Polynucleotides From Mononucleotides", filed 12 Dec. 2007, herein incorporated by reference in its entirety for all purposes.

This invention was made partly using funds from the U.S. National Human Genome Research Institute grant number HG003703-01. The US Federal Government has certain rights to this invention.

FIELD OF THE INVENTION

The invention herein disclosed provides for methods for the synthesis of polymers from monomers. In particular the method provides for the synthesis of polynucleotides from mononucleotides in the absence of catalytic enzymes. The invention is of particular use in the fields of molecular biology, structural biology, cell biology, molecular switches, molecular circuits, and molecular computational devices, and the manufacture thereof.

BACKGROUND

The invention relates to the field of compositions, methods, and apparatus for synthesizing and characterizing polymers, including polynucleotides.

Synthesis of macromolecules for use in biological studies, in the preparation of drugs for treatment of disease and disorders, for example polynucleotides encoding antibodies, growth factors, cytokines, or the like, for use in diagnoses of conditions, disease and disorders, currently utilize multi-molecular systems, such as chemical, biochemical, and cellular systems, that frequently require purified enzymes, reagents, and co-factors, thereby incurring significant cost in both monetary and temporal measures. In general, once used, most of the reagents are rendered unusable, being contaminated and/or degraded during the synthesis processes.

There is therefore a need in the art to provide a simple system wherein single monomers may be combined to create polymers under low energy constraints using few and/or simple, inexpensive, reagents.

The following studies on the origins of enzymatic and non-enzymatic hydrolysis of covalent and ionic bonds in a self-organizing system (i.e. "life"), usually under standard temperature and pressure (STP) or at temperature and pressure extremes, such as might occur in a prebiotic environment or in geological formations, disclose methods that have been shown to be particularly relevant to identifying how this need may be fulfilled.

Several studies have investigated possible pathways for the synthesis and degradation of RNA under hydrothermal conditions (White (1984) Nature 310: 430-432; Larralde et al. (1995) Proc. Natl. Acad. Sci. USA 92: 8158-8160; Miller and Lazcano (1995) J. Mol. Evol. 41: 689-692; Kawamura et al. (1997) Viva Origino 25: 177-190; Levy and Miller (1998) Proc. Natl. Acad. Sci. USA 95: 7933-7938; Kawamura (2004) Intl. J. Astrobiol. 3: 301-309). Kawamura's results suggest that it is possible for synthesis of phosphodiester bonds to occur in hot aqueous solutions if chemically activated monomers and catalysts are present. We have previously shown that lipid vesicles can encapsulate oligomerization reactions (Chakrabarti et al. (1994) J. Mol. Evol. 39: 555-559) and can also provide an organizing template for the non-enzymatic polymerization of thioglutamic acid to peptides (Zepik et al. (2007) Orig. Life Evol. Biosph. Mar. 25, 2007 (E-publication ahead of print)).

Because polymerization by condensation is thermodynamically unfavorable in aqueous solutions, an energy source is required to drive phosphodiester bond formation. Imidazole esters of mononucleotides are commonly used as activated monomers and readily assemble on RNA templates to produce complementary RNA strands up to 30 nucleotides in length (Inoue and Orgel (1983) Science 219: 859-862; Orgel (1998) Orig. Life Evol. Biosphere 28: 227-234). Huang and Ferris (Huang and Ferris (2003) Chem. Commun. 21: 1458-1461) and Ferris (2002, supra) found that the mineral surfaces of montmorillonite clay can organize chemically-activated mononucleotides so that RNA-like polymer chains in the 6-14 mer range are synthesized in the absence of templates, and up to 40-50 mers if a 10 mer is added as a primer or 1-methyladenine is used to activate the phosphate group of mononucleotides (Huang and Ferris (2006) J. Am. Chem. Soc. 128: 8914-8919).

These conditions are useful models for investigating non-enzymatic polymerization mechanisms, but a plausible source of activated monomers in the prebiotic environment remains elusive. For this reason we are investigating other conditions that could drive polymer synthesis. We first note that phosphodiester bond formation is a relatively low-energy reaction. It was estimated that the standard free energy of synthesis is +5.3 kcal/mol (Dickson et al. (2000) J. Biol. Chem. 275: 15828-15831) that is similar to that of glucose-1-phosphate formation (+5.0 kcal/mol) from glucose and phosphate in solution. Thus, it should be possible to drive phosphodiester bond formation in the absence of activated substrates by producing conditions in which water can be removed from the reactants. More recently, Kawamura (2002, Anal. Sci. 18: 715-716) developed a method to monitor RNA synthesis and degradation of RNA under simulated hydrothermal vent conditions, and demonstrated that the rate of phosphodiester bond formation was faster than the rate of decomposition at 100° C., but at higher temperature ranges (200 and 300° C.) degradation rates far exceeded synthesis. These results set an upper limit on thermal conditions for the origin of life, but also made it clear that there are no thermodynamic or kinetic barriers to RNA synthesis and stability in hyperthermophilic organisms like the chemolithoautotrophic archaeon Pyrolobus fumarii, which has been shown to be able to grow at 110° C. (Stetter (1999) FEBS Lett. 452: 22-25). Other extremophiles have also been found not only to survive but to thrive at such high temperatures (Stetter (1982) Nature 300: 258-260; Kashefi and Lovely (2003) Science 301: 934).

There is currently a need to provide compositions and methods that can be used in synthesis of polymers, including polynucleotides and polypeptides.

BRIEF DESCRIPTION OF THE INVENTION

The invention provides a method for synthesizing long chain polymers using monomer substrates, natural and synthetic phospholipids, under various aqueous, temperature, and temporal conditions. In one preferred embodiment, the polymer is a polynucleotide. In an alternative preferred embodiment, the polymer is a polypeptide. Other polymers that may be synthesized according to the invention include, but are not limited to, phospholipids, polysaccharides, and polyketides.

In one embodiment the invention provides a method for synthesizing a polymer, the method comprising: (i) providing an aqueous solution of phospholipid and monomer, wherein the solution comprises a plurality of phospholipid molecules and monomer molecules; (ii) subjecting the aqueous solution to fluctuating temperature conditions; (iii) subjecting the aqueous solution to fluctuating cycles of drying and hydrating conditions; (iv) subjecting the aqueous solution to fluctuating [$H^+$] conditions; (v) the fluctuating conditions thereby allowing formation of a chemical bond between at least two monomers thereby synthesizing a polymer. In a preferred embodiment the phospholipids comprise lipid multilayers. In a more preferred embodiment the lipid multilayers impart an ordering microenvironment that fuels non-enzymatic catalysis of monomers to produce a polymer.

In one embodiment, the polymer comprises biological activity. The polymer having biological activity can be, for example, but not limited to, proteins, peptides, antibodies, antigens, nucleic acids, peptide nucleic acids (PNAs), locked nucleic acids (LNAs), aptamers, morpholinos, sugars, lipids, glycophosphoinositols, lipopolysaccharides, or the like. The polymer can have antigenic activity. The polymer can have selective binding properties whereby the polymer binds to the compound under a particular controlled environmental condition, but not when the environmental conditions are changed. Such conditions can be, for example, but not limited to, change in [$H^+$], change in ambient temperature, change in stringency, change in hydrophobicity, change in hydrophilicity, change in percentage aqueous phase, or the like.

In one preferred embodiment, the aqueous solution is from between about 5% v/v water and about 100% v/v water. For example, the percentage of the aqueous solution can be about 5% v/v water, it can be about 10% v/v water, it can be about 15% v/v water, it can be about 20% v/v water, it can be about 25% v/v water, it can be about 30% v/v water, it can be about 35% v/v water, it can be about 40% v/v water, it can be about 45% v/v water, it can be about 50% v/v water, it can be about 55% v/v water, it can be about 60% v/v water, it can be about 65% v/v water, it can be about 70% v/v water, it can be about 75% v/v water, it can be about 80% v/v water, it can be about 85% v/v water, it can be about 90% v/v water, it can be about 95% v/v water, it can be about 99% v/v water, and it can be about 100% v/v water. In another preferred embodiment, the ambient temperature is from between about 20° C. and about 100° C. For example, the ambient temperature can be about 20° C., it can be about 25° C., it can be about 30° C., it can be about 33° C., it can be about 35° C., it can be about 37° C., it can be about 39° C., it can be about 40° C., it can be about 42° C., it can be about 45° C., it can be about 50° C., it can be about 55° C., it can be about 60° C., it can be about 65° C., it can be about 70° C., it can be about 75° C., it can be about 80° C., it can be about 85° C., it can be about 90° C., it can be about 95° C., it can be about 98° C., it can be about 100° C. In another preferred embodiment, [$H^+$] is from between about $10^{-2}$ M and about $10^{-8}$ M. For example, the [$H^+$] can be about $10^{-2}$ M, it can be about $5 \times 10^{-2}$ M, it can be about $10^{-3}$ M, it can be about $5 \times 10^{-3}$ M, it can be about $10^{-8}$ M, it can be about $5 \times 10^{-4}$ M, it can be about $10^{-5}$ M, it can be about $5 \times 10^{-5}$ M, it can be about $10^{-6}$ M, it can be about $5 \times 10^{-6}$ M, it can be about $10^{-7}$ M, it can be about $5 \times 10^{-7}$ M, or it can be about $10^{-8}$ M.

The mole ratio of monomer to phospholipid can be, for example, from between 1:1, 2:1, 3:1, 4:1, 5:1, 6:1, 7:1, 8:1, 9:1, 10:1, 15:1, 20:1, 25:1, 30:1, 40:1, 50:1, 100:1 and any amount therebetween.

In another preferred embodiment the phospholipid is selected from the group consisting of palmitoyl-oleoylphosphatidylcholine (POPC), palmitoyl-oleoylphosphatidic acid (POPA), lysophosphatidylcholine (LPC), phosphatidylcholine (PC), phosphatidylglycerol (PG), phosphatidylinositol (PI), phosphatidylethanolamine (PE), phosphatidylserine (PS), and sphingomyelin (SM).

In another alternative embodiment, the aqueous phase can further comprise a fatty acid, such as, but not limited to, lipids, diacylglycerol, triacylglycerol, long-chain fatty acids, arachidonic acid, eicosanoids, and palmitic acid.

In a still further preferred embodiment, the monomer is selected from the group consisting of adenosine 5'-monophosphate, uridine 5'-monophosphate, cytosine 5'-monophosphate, guanosine 5'-monophosphate, deoxyadenosine 5'-monophosphate, deoxycytosine 5'-monophosphate, deoxyguanosine 5'-monophosphohate, and thymidine monophosphate.

In an alternative embodiment the monomer is selected from the group consisting of inosine, inosinate, polyadenylic acid, polyuridylic acid, polycytidylic acid, polyguanidylic acid, polythymidylic acid, deoxyadenosine 5'-triphosphate, deoxyguanosine 5'-triphosphate, deoxycytidine 5'-triphosphate, deoxythymidine 5'-triphosphate, deoxyinosine 5'-triphosphate dideoxyadenosine 5'-triphosphate dideoxyguanosine 5'-triphosphate, dideoxycytidine 5'-triphosphate, dideoxythymidine 5'-triphosphate, and dideoxyinosine 5'-triphosphate.

In a more preferred embodiment, the chemical bond is a phosphodiester bond between at least two nucleotides, the method thereby synthesizing a polynucleotide.

In an alternative preferred embodiment, the monomer is an amino acid selected from the group consisting of alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine.

In another more preferred embodiment the chemical bond is a peptide bond between at least two amino acids, the method thereby synthesizing a polypeptide.

In an alternative embodiment the method further the step of adding to the aqueous solution a polypeptide, the polypeptide selected from the group consisting of amphipathic polypeptides, surfactant proteins, defensins, protegrins, dermaseptins, and NK-lysin.

In yet another embodiment the method further comprises the step of adding a cofactor, wherein the cofactor is selected from the group consisting of $Mg^{2+}$, $Mn^{2+}$, $Ca^{2+}$, ATP, $NAD^+$, $NADP^+$, diacylglycerol, phosphatidylserine, eicosinoids, retinoic acid, calciferol, ascorbic acid, neuropeptides, enkephalins, endorphins, 4-aminobutyrate (GABA), 5-hydroxytryptamine (5-HT), catecholamines, acetyl CoA, S-adenosylmethionine, hexose sugars, pentose sugars, phospholipids, lipids, glycosyl phosphatidyl inositols (GPIs), and any other biological cofactor.

In one preferred embodiment, the method comprises replication of a single-stranded polynucleotide template using a non-activated substrate, for example, a nucleoside monophosphate. In another preferred embodiment, the method comprises amplification of a single-stranded polynucleotide template using a non-activated substrate, for example, a nucleoside monophosphate.

In another embodiment the invention provides a method for synthesizing a polymer using non-enzymatic catalysis, the method comprising: (i) providing an aqueous solution of a template, phospholipid, and non-activated substrate; (ii) subjecting the aqueous solution to fluctuating temperature; (iii) subjecting the aqueous solution to fluctuating cycles of drying and hydrating; (iv) subjecting the aqueous solution to fluctuating [$H^+$]; (v) forming a chemical bond between the template and at least one non-activated substrate; (vi) forming a chemical bond between the bonded template and non-activated substrate and at least one more non-activated substrate thereby synthesizing a polymer using non-enzymatic catalysis. In a preferred embodiment the template is selected from the group comprising a single-stranded polynucleotide, an oligopeptide, and an oligosaccharide. In another preferred embodiment the non-activated substrate is selected from the group consisting of adenosine 5'-monophosphate, uridine 5'-monophosphate, cytosine 5'-monophosphate, guanosine 5'-monophosphohate, deoxyadenosine 5'-monophosphate, deoxycytosine 5'-monophosphate, deoxyguanosine 5'-monophosphohate, and thymidine monophosphate.

In another embodiment the invention provides a method for replicating a polymer template using non-enzymatic catalysis, the method comprising: (i) providing a polymer template; (ii) providing an aqueous solution of phospholipid and monomer, the aqueous solution in fluid communication with the polymer template; (iii) subjecting the aqueous solution to fluctuating temperature; (iv) subjecting the aqueous solution to fluctuating cycles of drying and hydrating; (v) subjecting the aqueous solution to fluctuating [H$^+$]; (vi) forming a chemical bond between at least two monomers, the two monomers corresponding to a portion of the polymer template, thereby replicating a polymer template using non-enzymatic catalysis. In a preferred embodiment the template is selected from the group comprising a single-stranded polynucleotide, an oligopeptide, and an oligosaccharide. In one preferred embodiment, the monomer is selected from the group consisting of adenosine 5'-monophosphate, uridine 5'-monophosphate, cytosine 5'-monophosphate, guanosine 5'-monophosphohate, deoxyadenosine 5'-monophosphate, deoxycytosine 5'-monophosphate, deoxyguanosine 5'-monophosphohate, and thymidine monophosphate.

In another embodiment, the invention provides a method for amplifying a polymer template using non-enzymatic catalysis, the method comprising: (i) providing a polymer template; (ii) providing an aqueous solution of phospholipid and monomer, the aqueous solution in fluid communication with the polymer template; (iii) subjecting the aqueous solution to fluctuating temperature; (iv) subjecting the aqueous solution to fluctuating cycles of drying and hydrating; (v) subjecting the aqueous solution to fluctuating [H$^+$]; (vi) forming a chemical bond between at least two monomers, the two monomers corresponding to a portion of the polymer template; (vii) repeating steps (iii) through (vi) thereby amplifying a polymer template using non-enzymatic catalysis. In one preferred embodiment, the template is selected from the group comprising a single-stranded polynucleotide, an oligopeptide, and an oligosaccharide. In another preferred embodiment, the monomer is selected from the group consisting of adenosine 5'-monophosphate, uridine 5'-monophosphate, cytosine 5'-monophosphate, guanosine 5'-monophosphohate, deoxyadenosine 5'-monophosphate, deoxycytosine 5'-monophosphate, deoxyguanosine 5'-monophosphohate, and thymidine monophosphate.

In another additional embodiment, the method comprises a step of subjecting the aqueous solution to fluctuating pressure conditions. In one embodiment, the pressure is from between about 0.1 kPa and about 100 MPa. For example, the pressure can be about 0.1 kPa, it can be about 0.5 kPa, it can be about 1 kPa, it can be about 5 kPa, it can be about 10 kPa, it can be about 50 kPa, it can be about 60 kPa, it can be about 70 kPa, it can be about 80 kPa, it can be about 90 kPa, it can be about 100 kPa, it can be about 105 kPa, it can be about 110 kPa, it can be about 120 kPa, it can be about 130 kPa, it can be about 140 kPa, it can be about 150 kPa, it can be about 160 kPa, it can be about 170 kPa, it can be about 180 kPa, it can be about 190 kPa, it can be about 200 kPa, it can be about 250 kPa, it can be about 300 kPa, it can be about 350 kPa, it can be about 400 kPa, it can be about 450 kPa, it can be about 500 kPa, it can be about 600 kPa, it can be about 700 kPa, it can be about 800 kPa, it can be about 900 kPa, it can be about 1 MPa, it can be about 10 MPa, it can be about 20 MPa, it can be about 30 MPa, it can be about 40 MPa, it can be about 50 MPa, it can be about 60 MPa, it can be about 70 MPa, it can be about 80 MPa, it can be about 90 MPa, or it can be about 100 MPa. Under pressure greater than that of standard atmospheric pressure, the ambient temperature can be about 90° C., it can be about 95° C., it can be about 100° C., it can be about 120° C., it can be about 150° C., it can be about 200° C., it can be about 250° C., or it can be about 300° C.

BRIEF DESCRIPTION OF THE DRAWINGS

FIG. 3a shows an open channel current with no additions. FIG. 3b shows blockades produced by a known 50 mer of polyadenylic acid. FIGS. 3c and 3d show blockades produced by AMP:POPA and AMP:POPC reaction products. FIG. 3e shows the event amplitudes produced by oligomers of 5'-UMP. FIG. 3f shows that a mixture of all four nucleotides reacting in the presence of POPA.

In FIG. 4a, the mononucleotide to lipid ratios were 2:1 (POPC), 1:1 (LPC) and 2:1 (PUPA). In FIG. 4b the AMP to lipid ratio was 2:1.

FIG. 5a shows one such series in which the number of cycles was varied, using AMP and POPC in a 2:1 mole ratio. Lane A: air was used instead of carbon dioxide during drying (7 cycles). Lane B: Lipid absent (7 cycles). Lane C: unheated control. Lane D: 10 µg of commercial polyadenylic acid as a positive control for the end labeling process. Lane E shows an RNA ladder containing known lengths of RNA in 10 nucleotide (nt) increments. FIG. 5b shows the three temperature ranges tested. FIG. 5c shows the results for three lipids tested. FIG. 5d illustrates how the nucleotide to lipid ratio affects chain length and apparent yield. FIG. 5e shows the effect of substituting UMP for AMP.

FIG. 12.1 shows a mixture of dAMP, dCMP, dTMP and dGMP (sample 1).

FIG. 12.2 shows a mixture of template and unreacted mononucleotides (sample 2).

FIG. 12.3 shows product of the abiotic reaction in the absence of template (sample 3).

FIG. 12.5 shows product of the abiotic reaction in the presence of template (sample 5).

FIG. 12.E shows the result when 64mer oligomer DNA used as a template.

FIG. 14A: Lane 1 was digested for 2 hours at 37° C.; Lane 2 was not digested; Lane 3 is the $M_w$ ladder. FIG. 14B illustrates the scan of each lane: upper scan—No Digestion; middle scan—2h at 37° C.; lower scan—Ladder.

FIG. 15a: The product of the reaction extends completely to the full length of the template. FIG. 15b: The multiple sized products of the abiotic reaction pair flat at different locations of the template covering most of its length. FIG. 15c: The products of the abiotic reaction pair forming some structure at different locations of the template covering most of its length.

DETAILED DESCRIPTION OF THE INVENTION

Figure 1:
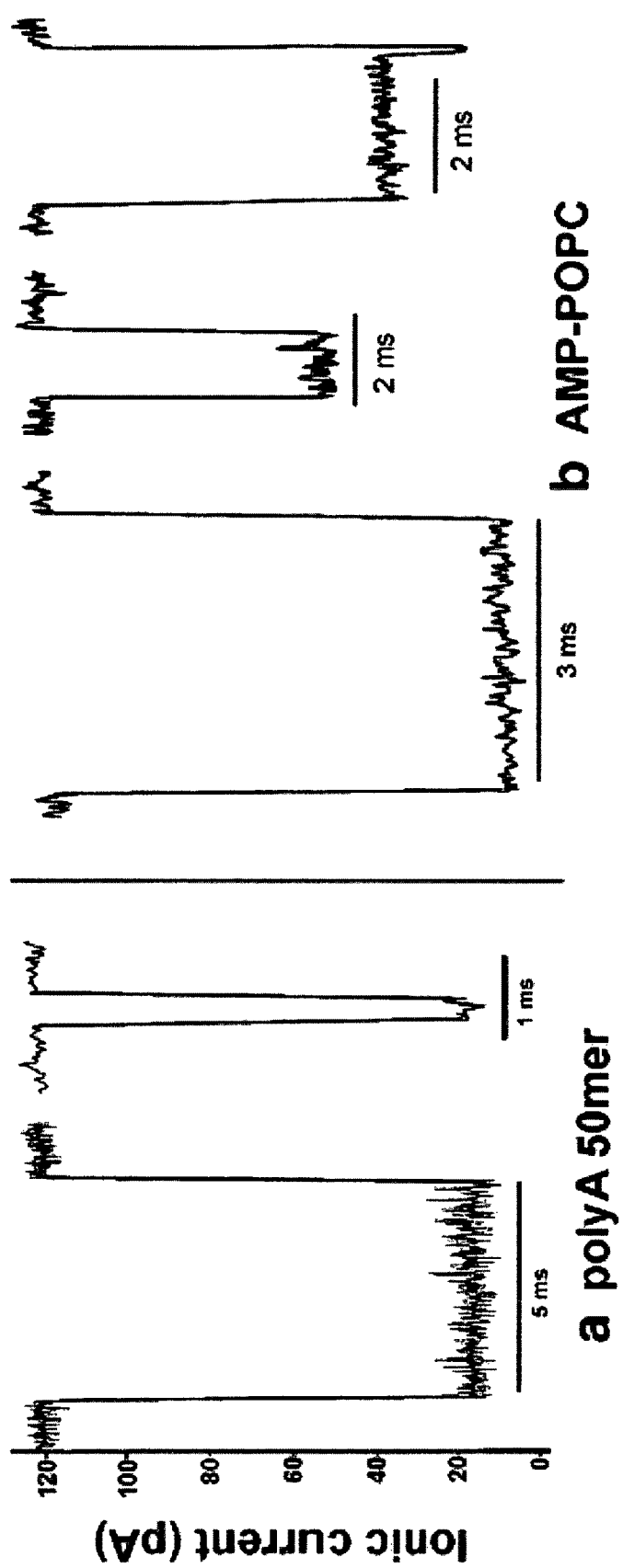
FIG. 1 illustrates nanopore analysis of RNA-like products.

The embodiments disclosed in this document are illustrative and exemplary and are not meant to limit the invention. Other embodiments can be utilized and structural changes can be made without departing from the scope of the claims of the present invention. Here we report that the organizing effect of lipid systems can promote synthesis of RNA-like oligomers from non-activated 5'-nucleoside monophosphates. The methods disclosed herein may be used with or without a template molecule. The methods disclosed herein can also be used for the synthesis of other nucleotides, such as DNA, peptide nucleic acids, and the like.

As used herein and in the appended claims, the singular forms "a," "an," and "the" include plural reference unless the context clearly dictates otherwise. Thus, for example, a reference to "a monomer" includes a plurality of such monomers, and a reference to "a bond" is a reference to one or more bonds and equivalents thereof, and so forth.

DEFINITIONS

"Fragment" refers to a chain of consecutive nucleotides from about 10 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, for example, 5'-A-G-T-C-3' base pairs with 3'-T-C-A-G-5'.

Hybridization conditions, degree of complementarity and the use of nucleotide analogs affect the efficiency and stringency of hybridization reactions.

"Labeling moiety" refers to any visible or radioactive label than can be attached to or incorporated into a polynucleotide or protein. Visible labels include but are not limited to anthocyanins, green fluorescent protein (GFP), β glucuronidase, luciferase, Cy3 and Cy5, and the like. Radioactive markers include radioactive forms of hydrogen, iodine, phosphorous, sulfur, and the like.

"Ligand" refers to any agent, molecule, or compound that binds specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers to a single-stranded molecule comprising from about 18 to about 60 nucleotides in length that may be used in hybridization or amplification technologies or in regulation of replication, transcription or translation. Equivalent terms are amplimer, primer, and oligomer.

An "oligopeptide" is an amino acid sequence from about five residues to about 15 residues that can be used as part of a fusion protein to produce an antibody By "polynucleotide" is meant DNA or RNA, including any naturally occurring, synthetic, or modified nucleotide. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, 2-thiocytidine as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

The term "incompatible" refers to the chemical property of a molecule whereby two molecules or portions thereof cannot interact with one another, physically, chemically, or both. For example, a portion of a polymer comprising nucleotides can be incompatible with a portion of a polymer comprising nucleotides and another chemical moiety, such as for example, a peptide nucleic acid, a 2'-O-methyl group, a fluorescent compound, a derivatized nucleotide, a nucleotide isomer, or the like. In another example, a portion of a polymer comprising amino acid residues can be incompatible with a portion of a polymer comprising amino acid residues and another chemical moiety, such as, for example, a sulfate group, a phosphate group, an acetyl group, a cyano group, a piperidine group, a fluorescent group, a sialic acid group, a mannose group, or the like.

"Alignment" refers to a number of DNA or amino acid sequences aligned by lengthwise comparison so that components in common (such as nucleotide bases or amino acid residues) may be visually and readily identified. The fraction or percentage of components in common is related to the homology or identity between the sequences. Alignments may be used to identify conserved domains and relatedness within these domains. An alignment may suitably be determined by means of computer programs known in the art, such as MACVECTOR software (1999) (Accelrys, Inc., San Diego, Calif.).

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Polynucleotide hybridization methods are disclosed in detail by Kashima et al. (1985) Nature 313: 402-404, and Sambrook et al. (1989) Molecular Cloning: A Laboratory Manual, 2nd Ed., Cold Spring Harbor Laboratory, Cold Spring Harbor, N.Y. ("Sambrook"); and by Haymes et al., "Nucleic Acid Hybridization: A Practical Approach", IRL Press, Washington, D.C. (1985), which references are incorporated herein by reference.

In general, stringency is determined by the incubation temperature, ionic strength of the solution, and concentration of denaturing agents (for example, formamide) used in a hybridization and washing procedure (for a more detailed description of establishing and determining stringency, see below). The degree to which two nucleic acids hybridize under various conditions of stringency is correlated with the extent of their similarity. Thus, similar polynucleotide sequences from a variety of sources, such as within an organism's genome (as in the case of paralogs) or from another organism (as in the case of orthologs) that may perform similar functions can be isolated on the basis of their ability to hybridize with known peptide-encoding sequences. Numerous variations are possible in the conditions and means by which polynucleotide hybridization can be performed to isolate sequences having similarity to sequences known in the art and are not limited to those explicitly disclosed herein. Such an approach may be used to isolate polynucleotide sequences having various degrees of similarity with disclosed sequences, such as, for example, sequences having 60% identity, or more preferably greater than about 70% identity, most preferably 72% or greater identity with disclosed sequences.

Synthesis of Polymers from Monomers Using Simple Substrates

Here we show that RNA-like polymers can be synthesized non-enzymatically from mononucleotides in lipid environments. The synthesis of the RNA-like polymers was confirmed by standard methods of enzymatic end labeling followed by gel electrophoresis and nanopore analysis. Chemical activation of the mononucleotides is not required. Instead, synthesis of phosphodiester bonds is driven by the chemical potential of fluctuating anhydrous and hydrated conditions, with heat providing activation energy during dehydration. In the final hydration step, the RNA-like polymer is encapsulated within lipid vesicles. This process provides a laboratory model of an early stage of evolution toward an RNA World and may further be used to synthesize polynucleotides using inexpensive materials and reagents, thereby of benefit to those of skill in the art.

One particular advantage of the methods we disclose herein is that the method can use nucleoside monophosphates as non-activated substrates to synthesize, replicate, and/or amplify a polynucleotide. This is advantageous over the current use of triphosphate-containing compounds as substrates.

We investigated RNA synthesis at elevated temperature ranges in fluctuating environments simulating hydrothermal springs that were likely to have been common in the prebiotic Earth. In such environments, cycles of wetting and drying in principle have sufficient free energy to "pump" a mixture of simple molecules toward increasingly complex molecular systems. The drying process concentrates otherwise dilute organic solutes, and also produces a chemical potential that can drive synthetic reactions such as ester bond formation. The reason this does not ordinarily work is that potential reactants are disorganized and immobilized within the solid matrix of a dry film, so that reactive groups only rarely come into contact to undergo condensation reactions. However, if a microenvironment could be discovered that not only organized the mononucleotides but also permitted diffusional mobility, it is possible that oligonucleotides resembling RNA would be synthesized from their monomers.

To this end, we are investigating the properties of microenvironments produced by organized fluid lipid matrices (liquid crystals). Ordering effects of amphiphilic structures in promoting prebiotic RNA synthesis have recently been discussed by Walde (2006, Orig. Life Evol. Biosph. 109-150, Apr. 27, 2006 (E-publication ahead of print)). In past work, we have shown that solutes are trapped between the lamellae of lipid films when a mixture of lipid vesicles and a solute is dehydrated (Deamer and Barchfeld (1982) J. Mol. Evol. 18: 203-206). The vesicles fuse to form a multilamellar sandwich (e.g. multilayer phospholipids) in which alternate lamellae contains a thin layer of the original solute. We are now testing the hypothesis that fluid lipid microenvironments impose order on mononucleotides in such a way that they are able to form extensive phosphodiester bonds and thereby produce RNA-like polymers sufficiently long to have catalytic activity (Szostak et al. (2001) Nature 409: 387-390).

As disclosed herein, low yields of RNA-like polymers have been observed, typically 50 nucleotides in length and ranging in length from between about 10 to about 100 nucleotides. The ability of lipid matrices to add order to nucleotides is similar to the ordering effect of Montmorillonite clay surfaces (Huang (2006) supra; Ertem and Ferris (1996) Nature 379: 238-240). However, because the lipid matrices are liquid crystalline structures, potential reactants are able to diffuse within the two-dimensional plane. Furthermore, if water molecules are produced during a condensation reaction, they are able to escape through the lipid film and thereby reduce the potential for hydrolytic back reactions. The activation energy for phosphodiester bond formation would be provided by the relatively warm temperatures (70° C.-90° C.) of the prebiotic environment.

If random nucleic acid polymers can be spontaneously synthesized by simple condensation reactions, the next question is whether the same conditions are able to promote replication of an existing nucleic acid strand. We show here that nucleic acid molecules present in a mixture of nucleoside monophosphates and lipids can act as templates for the formation of complementary strands, which can then pair specifically with the template. In order to take advantage of the abundance of assays designed to analyze dsDNA in comparison to RNA, we used deoxyribonucleotides instead of ribonucleotides in the reaction mixture.

In another embodiment, the method can be used with amino acids to synthesize random peptide polymers (homopolymers) and specific peptide heteropolymers comprising a specific amino acid residue sequence. Such peptide homopolymers are well known to those of skill in the art, for example, poly-lysine, poly-arginine, poly-glutamate, and the like. Such peptide heteropolymers are well known to those of skill in the art, for example, Arg-Ala-Asp (RAD), Arg-Gly-Asp (RGD), enkephalins, endorphins, melanocyte-stimulating hormone, adrenocorticotropin, thyrotropin-releasing hormone (TRH), gonadotropin-releasing hormone (GNRH), biologically active variants thereof, and other peptides or proteins having biological activity such as compounds comprising PDZ domains, KDEL (SEQ ID NO: 1), ROD, NGR, and GSL sequence motifs, von Willebrand factor A (vWFA) domains, and EGF-like domains, RGD, NGR, and GSL motif-containing peptides.

Exemplary Uses of the Invention

Synthesis of Polymers

Synthesis of polynucleotides, both DNA and/or RNA, may now be performed using the methods disclosed herein. The methods are advantageous in that the reagents are generally readily available, the reaction conditions are easily controllable, and the product can be readily processed and purified from the reaction mixtures using any one of the methods disclosed herein. The nucleotide sequence of the polynucleotide may controlled and/or predetermined by using a single stranded template of known sequence in combination with the lipid catalyst. For example, the single stranded template may be an oligonucleotide, it may be an oligopeptide, or it may be an oligosaccharide. The methods disclosed herein may be used to ligate additional monomers to the single stranded template. The sequence of the resulting polymer can then be deduced using methods well known to those if skill in the art, such as DNA sequencing, including, but not limited to, Maxam-Gilbert sequencing, dideoxy (Sanger) sequencing, pyrosequencing, and variants thereof, amino acid sequencing, such as, for example, Edman degradation, CnBr/gel filtration/MS sequencing, and variants thereof.

The methods disclosed herein may also be used in combination with changes in the ambient pressure. For example, performing a reaction at high temperature, for example near or above 100° C. and at an ambient temperature lower than that of atmospheric pressure at sea level may result in an improved yield of polymer. For example, the method performed at 10 kPa and at 100° C. reduces sublimation of the aqueous phase and therefore formation of bonds between monomers may be more likely to occur. Sublimation of the aqueous phase at elevated temperatures (>90° C.) may also be reduced if the method is performed under conditions of high pressure, for example at 200 kPa, whereby the increased pressure prevents evaporation of the aqueous phase and may better mimic environmental conditions at geological depth. As reference, the standard atmospheric pressure at sea level is 101.325 kPa (about 100 kPa).

Polynucleotides homologous to other polynucleotides may be identified by hybridization to each other under stringent or under highly stringent conditions. Single-stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited above.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$\text{DNA-DNA: } T_m(°\text{C.})=81.5+16.6(\log [\text{Na}^+])+0.41(\% G+C)-0.62(\% \text{ formamide})-500/L \quad \text{(I)}$$

$$\text{DNA-RNA: } T_m(°\text{C.})=79.8+18.5(\log [\text{Na}^+])+0.58(\% G+C)+-0.12(\% G+C)^2-0.5(\% \text{ formamide})-820/L \quad \text{(II)}$$

$$\text{RNA-RNA: } T_m(°\text{C.})=79.8+18.5(\log [\text{Na}^+])+0.58(\% G+C)+0.12(\% G+C)^2-0.35(\% \text{ formamide})-820/L \quad \text{(III)}$$

where L is the length of the duplex formed, [Na$^+$] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between pH 6.8 to 7.4, although the rate of hybridization is nearly independent of pH at ionic strengths likely to be used in the hybridization buffer (Anderson and Young (1985) "Quantitative Filter Hybridisation." In: Hames and Higgins, editors, Nucleic Acid Hybridisation. A Practical Approach. Oxford, IRL Press, 73-111). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll, and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt (for example, NaCl) concentration, formamide concentration, hybridization temperature and probe lengths are variables that can be used to alter stringency (as described by the formula above). As a general guidelines high stringency is typically performed at $T_m$–5° C. to $T_m$–20° C., moderate stringency at $T_m$–20° C. to $T_m$–35° C. and low stringency at $T_m$–35° C. to $T_m$–50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$–25° C. for DNA-DNA duplex and $T_m$–15° C. for RNA-DNA duplex. Optionally, the degree of dissociation may be assessed after each wash step to determine the need for subsequent, higher stringency wash steps.

High stringency conditions may be used to select for polynucleotide sequences with high degrees of identity to the disclosed sequences. An example of stringent hybridization conditions obtained in a filter-based method such as a Southern or northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. polynucleotide molecules that hybridize under stringent conditions will typically hybridize to a probe based on either the entire DNA molecule or selected portions, for example, to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, for example, formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, for example, sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing the wash temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the polynucleotide sequences or their complements that encode the present transcription factors include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 min, or about 0.1×SSC, 0.1% SDS at 65° C. and washing twice for 30 min. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, for example, 50° C.

An example of a low stringency wash step employs a solution and conditions of at least 25° C. in 30 mM NaCl, 3 mM trisodium citrate, and 0.1% SDS over 30 min. Greater stringency may be obtained at 42° C. in 15 mM NaCl, with 1.5 mM trisodium citrate, and 0.1% SDS over 30 min. Even higher stringency wash conditions are obtained at 65° C. to 68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (for example, in US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a polynucleotide encoding a transcription factor known as of the filing date of the application. It may be desirable to select conditions for a particular assay such that a higher signal to noise ratio, that is, about 15× or more, is obtained. Accordingly, a subject polynucleotide will hybridize to a unique coding oligonucleotide with at least a 2× or greater signal to noise ratio as compared to hybridization of the coding oligonucleotide to a polynucleotide encoding known polypeptide. The particular signal will depend on the label used in the relevant assay, for example, a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Chimeric Polymers

In some cases, it may be desirable to include compounds in the aqueous phase that are known to interact with biological membrane structures, including lipid bilayers and multilamellar bodies and organelles. Such compounds are well know to those of skill in the art and can include, but are not limited to, fatty acids such as, but not limited to, lipids, diacylglycerol, triacylglycerol, long-chain fatty acids, arachidonic acid, eicosanoids, palmitic acid, variants thereof or the like; polypeptide such as, but not limited to amphipathic polypeptides, surfactant proteins, defensins, protegrins, dermaseptins, NK-lysin, variants thereof, or the like; and other compositions such as, but not limited to glycosyl phosphatidyl inositols, peptidoglycans, sphingolipids, cholesterol, glycerophospholipids, variants thereof, or the like. Such compounds disclosed herein may be modified to be able form a chemical bond with any of the other compounds so disclosed, thereby creating chimeric polymer compounds that may be used in the production of pharmaceutical formulations.

It will be understood that such chemical bonds are not limited to a diester bond, a phosphodiester bond, or a peptide bond, and can include any bond that is the result of a condensation reaction. Bonds resulting from condensation reactions are well known to those of skill in the art.

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The polynucleotides, fragments, oligonucleotides, complementary RNA and DNA molecules, and PNAs may be used to detect and quantify altered gene expression, absence/presence versus excess, expression of mRNAs or to monitor mRNA levels during therapeutic intervention. Conditions, diseases or disorders associated with altered expression include idiopathic pulmonary arterial hypertension, secondary pulmonary hypertension, a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis; acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, benign prostatic hyperplasia, bronchitis, Chediak-Higashi syndrome, cholecystitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, chronic granulomatous diseases, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polycystic ovary syndrome, polymyositis, psoriasis, Reiter's syndrome, rheumatoid arthritis, scleroderma, severe combined immunodeficiency disease (SCID), Sjogren's syndrome, systemic anaphylaxis, systemic lupus erythematosus, systemic sclerosis, thrombocytopenic purpura, ulcerative colitis, uveitis, Werner syndrome, hemodialysis, extracorporeal circulation, viral, bacterial, fungal, parasitic, protozoal, and helminthic infection; a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis; cancer of the breast, fibrocystic breast disease, and galactorrhea; a disruption of spermatogenesis, abnormal sperm physiology, benign prostatic hyperplasia, prostatitis, Peyronie's disease, impotence, gynecomastia; actinic keratosis, arteriosclerosis, bursitis, cirrhosis, hepatitis, mixed connective tissue disease (MCTD), myelofibrosis, paroxysmal nocturnal hemoglobinuria, polycythemia vera, primary thrombocythemia, complications of cancer, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In another aspect, the polynucleotide of the invention.

The polynucleotides, fragments, oligonucleotides, complementary RNA and DNA molecules, and PNAs, or fragments thereof, may be used to detect and quantify altered gene expression; absence, presence, or excess expression of mRNAs; or to monitor mRNA levels during therapeutic intervention. Disorders associated with altered expression include akathesia, Alzheimer's disease, amnesia, amyotrophic lateral sclerosis, ataxias, bipolar disorder, catatonia, cerebral palsy, cerebrovascular disease Creutzfeldt-Jakob disease, dementia, depression, Down's syndrome, tardive dyskinesia, dystonias, epilepsy, Huntington's disease, multiple sclerosis, muscular dystrophy, neuralgias, neurofibromatosis, neuropathies, Parkinson's disease, Pick's disease, retinitis pigmentosa, schizophrenia, seasonal affective disorder, senile dementia, stroke, Tourette's syndrome and cancers including adenocarcinomas, melanomas, and teratocarcinomas, particularly of the brain. These cDNAs can also be utilized as markers of treatment efficacy against the diseases noted above and other brain disorders, conditions, and diseases over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

The diagnostic assay may use hybridization or amplification technology to compare gene expression in a biological sample from a patient to standard samples in order to detect altered gene expression. Qualitative or quantitative methods for this comparison are well known in the art.

For example, the polynucleotide or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate the level that is observed in a normal subject. The results obtained from successive assays may be used to show the efficacy of treatment over a period ranging from several days to months.

In additional embodiments, the polynucleotides may be used in any molecular biology techniques that have yet to be developed, provided the new techniques rely on properties of polynucleotides that are currently known, including, but not limited to, such properties as the triplet genetic code and specific base pair interactions.

Methods for Synthesis of Polymers

It is envisioned that many different chemical species of monomer may be polymerized using the methods disclosed herein. Chimeric polymers, comprising blocks of one chemical species and blocks of another different chemical species are also understood to be part of the invention. For example, a chimeric polymer may comprise oligopeptides and polymers of phospholipids, fatty acids, such as eicosanoids or arachidonic acid, and/or glycosylphosphatidylinositol anchors. Such chimeric polymers would be of use to target proteins, such as receptor ligands or G-proteins to a plasma cell membrane, for example. There are many such variants that can be envisioned by one of skill in the art and may also include combinations of aptamers, polysaccharides, and polyketides.

Fluctuating environments in the form of wet-dry cycles have long been considered as possible sources of free energy to drive uphill polymerization reactions (Kuhn (1976) Naturwiss. 63: 68-80; Odom et al. (1979) J. Mol. Evol. 12: 259-264; Lahav et al. (1978) Science 201: 67-69; Lahav (1999) Biogenesis: Theories of Life's Origins. Oxford University Press, New York N.Y.). Verlander et al. (1973, J. Mol. Evol. 2: 303) showed that anhydrous heating of nucleotides could drive the formation of mixed 2'-5' and 3'-5' phosphodiester bonds, yielding dimers and trimers. Usher (1977, Science 196: 311-313) proposed that cycles of heating and drying, followed by rehydration, could drive phosphodiester bond formation and promote the accumulation of 3'-5' bonds in the system due to the relative lability of 2'-5' bonds to hydrolysis. The RNA-like polymers reported here differ from those of earlier studies in that the range of chain lengths is significantly longer (25-100 nucleotides) and the reaction does not require nucleotide activation to occur.

The reaction conditions in which RNA-like polymers form are relatively complex, and further research will be required before a mechanism can be put forward. It is likely that the process somehow involves an ordering effect of the lipid phase, presumably arising from the fact that the nucleotides are present at very high concentrations within lipid structures in the dry phase of each cycle. The combination of high concentration of reactants, interaction with polar head groups of lipids, and stacking of purine and pyrimidine bases would tend to align nucleotide molecules in such a way that phosphodiester bond formation is favored. Although the precise mechanism is not yet understood, one possibility is that at low pH ranges an —OH group on the phosphate becomes protonated to —OH$_2^+$ which then becomes a potential leaving group. A neighboring 2' or 3' hydroxyl of a ribose then can undergo a nucleophilic attack on the phosphorus to produce an ester bond. The moderately elevated temperature of 60-90° C. provides activation energy for the reaction without significant degradation of reactants or products. Another possibility is that phosphodiester bond synthesis is driven by the initial formation of cyclic nucleotides that have sufficient stored energy in the internal diester bond to enter into polymerization reactions. These possibilities are now being investigated.

It may also be significant that, in contrast to the solid surface of a mineral such as clay, the lipid microenvironment is composed of fluid lipids. The diffusional mobility of mononucleotides adsorbed to a polar mineral surface such as clay would be markedly reduced, which would tend to slow reaction rates. However, reactant molecules captured within a fluid lipid matrix are able to diffuse and interact, which would promote covalent bond synthesis by condensation reactions. Another important difference between a multilamellar lipid phase and a solid bulk phase film of mononucleotides is that water molecules readily permeate lipid bilayers and are lost to the atmosphere, thereby reducing potential hydrolytic back reactions. In a solid bulk phase, water molecules cannot readily diffuse away from the reaction site.

The fact that lysophosphatidylcholine (LPC) also promoted polymerization of mononucleotides suggested an interesting possibility. In designing the experiments, we assumed that the nucleotide monomers would be present as 2-dimensional films between lipid bilayers. But LPC in dry or partially hydrated states forms a hexagonal I phase, in which the lipid molecules are arranged as cylinders around a central axis with head groups directed outward and tails inward (Reiss-Husson (1967) J. Mol. Biol. 25: 363-382). The term 'hexagonal' refers to the packing of the cylinders, which have an axis-to-axis spacing of 5 nm. In this structure, the mononucleotides would not occupy a 2-dimensional space, but instead would line up single file in the volume between the hexagonally packed cylinders. X-ray diffraction studies of lipid phases that have incorporated solutes during drying have not been carried out, particularly at elevated temperatures, but it seems possible that LPC and perhaps POPC and POPA exist in hexagonal phases when dried in the presence of solutes at elevated temperatures. This means that entrapped solutes such as AMP and UMP would be present in one-dimensional linear arrays, which would further order the molecular aggregates and thereby promote polymerization by phosphodiester bond formation.

It is perhaps surprising that polymeric products are able to survive the conditions of the cycling used here to drive polymer synthesis. For instance, at pH 3 and 100° C., conditions similar to those used in our experiments, 10% of biological RNA in solution is hydrolyzed in 40 min (Stanley (1968) Meth. Enzymol. 12: 404-407). In control experiments in the absence of lipid and mononucleotides, we found that polyadenylic acid is in fact hydrolyzed to monomers and oligomers after several cycles. However, polyadenylic acid in the presence of lipid was markedly less affected by these conditions, and after three cycles approximately 25% or the initial quantity remained. A certain amount of hydrolysis presumably does occur in the hydrated stage of a cycle, but when mononucleotides are present the forward reaction of phosphodiester bond synthesis would also occur in the anhydrous stage, with the net effect of preserving longer polymers. Kawamura and colleagues investigated the formation and stability of phosphodiesters bond at elevated temperatures (Kawamura et al. (1997) supra; Kawamura (2004) Intl. J. Astrobiol. 3: 301-309). Their findings show that net synthesis of oligonucleotides from activated mononucleotides can occur at 100° C. because rates of formation of phosphodiester bonds at elevated temperatures exceed hydrolysis rates. This result is consistent with the observation reported here, that surprisingly long strands of RNA are maintained after synthesis at low pH and 90° C.

To summarize, lipid microenvironments are able to organize mononucleotides within a lipid matrix when phospholipid vesicles are mixed with mononucleotides and dried. Under these conditions, long strands of RNA-like molecules are synthesized by a condensation reaction when the reactants are exposed to one or more cycles of dehydration and elevated temperatures, followed by rehydration. The chemical potential driving the reaction is presumably supplied by the anhydrous conditions, with heat providing activation energy. At the end of the reaction, the polymers are encapsulated in vesicles formed by the lipid upon rehydration.

In conclusion, we have demonstrated that nucleic acid molecules can act as templates in the synthesis of complementary nucleic acids under conditions simulating a fluctuating prebiotic environment. Such environments are characterized by cycles of hydration and dehydration, with modest heat (90° C.) available to provide activation energy. In these conditions, and in acidic pH ranges, a chemical potential exists that can drive phosphodiester bond formation by simple condensation reactions in which water molecules become leaving groups. The sequence of the template used in our model system was defined by the linearity of DNA required for analytical purposes. However, the polymerization reaction is independent of the template sequence and has the potential to provide molecular heredity through replication of informational molecules. This process would have been especially relevant in the early stages leading to the origin of life, where an imperfect replication would have allowed the exploration of the sequence space and eventually, the appearance of functional nucleic acid sequences. This reaction system described here establishes a causal connection between vesicle-forming lipid molecules and information-carrying macromolecules. In this way, nucleic acid-driven biological processes could have been encapsulated within individual vesicles, which then as populations had the capacity to evolve toward increasingly complex molecular systems. One such system, yet to be elucidated, represented the step between non-living molecular assemblages and the first compartmented systems of macromolecules that we would recognize as living cells.

The invention will be more readily understood by reference to the following examples, which are included merely for purposes of illustration of certain aspects and embodiments of the present invention and not as limitations.

EXAMPLES

Herein are described several examples to demonstrate the capability of measuring macromolecules and polanions or polycations.

Example I

Preparation of Lipid Dispersions

Materials

Mononucleotides (adenosine 5'-monophosphate and uridine 5'-monophosphate guanosine 5'-monophosphate and cytidine 5'-monophosphate), polyadenylic acid and polyuridylic acid were purchased from Sigma-Aldrich. The lipids, POPC (palmitoyl-oleoylphosphatidylcholine), POPA (palmitoyl-oleoylphosphatidic acid) and LPC (lysophosphatidylcholine) were purchased from Avanti Polar Lipids Inc. All other reagents were of analytical grade from Fisher, Sigma-Aldrich and Avanti Polar Lipids Inc.

Phosphatidylcholine (POPC) was injected as a 20 mM solution in ethanol into the aqueous phase to produce small unilamellar vesicles (Batzri and Korn (1973) Biochim. Biophys. Acta 298: 1015-1019). Phosphatidic acid (POPA) and lysophosphatidylcholine (LPC enzymatically prepared from egg yolk phosphatidylcholine) were dispersed by 1 min agitation in a vortex stirrer. The lipid concentration was typically 10 mg/ml, and additions of AMP, UMP or 1:1 AMP:UMP mixtures (as 5'-mononucleoside phosphates) were adjusted to the desired mole ratio. For example, 10 mg/ml of POPC is 0.013 M and 10 mg/ml of AMP has a molarity of 0.027 M. In order to get a 1:2 molar ratio of POPC: AMP about equal volumes of 10 mg/ml stock solutions of each was added to the reaction setup.

Reaction Conditions

Mononucleotides and lipids (mole ratios of mononucleotide to lipid 2:1. 4:1 and 8:1) were mixed and put through a series of hydration-dehydration cycles to simulate a fluctuating environment on the prebiotic Earth. In a typical reaction the reactants were exposed to 1-7 cycles of wetting and drying in a volume of 0.5 ml. A stream of carbon dioxide (or in some experiments nitrogen gas) was used to dry the samples while they were exposed to varying experimental parameters including temperature (60-90° C.), time (30-120 min), lipid composition and mole ratio of mononucleotide to lipid. After each drying cycle the samples were dispersed in 1 mM HCl and allowed to rehydrate for 15-20 min. During this time lipid vesicles reformed and components underwent mixing, and the mixtures were then exposed to a further dehydration cycle. The starting pH was 6.8, and this decreased to 2.2 at the end of seven cycles. When the cycle series was complete, the samples were dispersed in water, and the lipids were extracted twice with n-butanol (2:1 by volume) followed by hexane to remove excess remaining butanol. Some of the untreated samples were set aside for examination by light microscopy.

Example II

Gel Electrophoresis: $^{32}$P-Labeling and Analysis of Reaction Products

After lipid extraction, samples were ethanol-precipitated and dissolved in 44 μl of water. For dephosphorylation, 1 μl of calf intestinal alkaline phosphatase (CIAP, 1 U/μl, MBI Fermentas) was added along with 5 μl of 10×CIAP buffer, and the reaction was incubated at 37° C. for 30 min, followed by phenol extraction and ethanol precipitation. Glycogen (1 μl of stock 20 mg/ml) was added to facilitate precipitation of small amounts of RNA. The RNA aggregates were pelleted by centrifugation, then dissolved in 16 μl of water and labeled at the 5'-termini with $^{32}$P. Phosphorylation was carried out by adding 1 μl of T4 polynucleotide kinase (T4 PNK, 10 U/μl, New England Biolabs), 2 μl of 10×PNK buffer and 1 μl γ-[32P]ATP, followed by incubation at 37° C. for 15 min. The end-labeled RNA-like polymers were purified by G50 spin columns (Amersham Biosciences) and stored at −20° C. For gel electrophoresis, 10 μl aliquots of the RNA samples were mixed with 3× denaturing loading solution (7 M urea, 10 mM EDTA, and 0.02% xylene cyanol and bromphenol blue) and separated by electrophoresis on 15% polyacrylamide gels containing 7 M urea, along with Molecular Weight (MW) markers.

Reaction yields were determined by performing RiboGreen assays. The assay kit was obtained from BioTek Instruments, Inc., Winooski, Vt. The RiboGreen RNA quantitation assay is a very sensitive technique that can detect as little as 1 ng/mL RNA. A standard curve was first obtained for polyadenylic acid and was used to estimate the yields obtained in the experimental samples.

Example III

HPLC Analysis

HPLC analysis was performed by reverse phase chromatography employing an Alltima C-18 (5 μm) column (250 mm×4.6 mm) on a Waters HPLC system. The samples were run at a flow rate of 0.5 ml/min in a water/acetonitrile gradient containing 0.1% trifluoroacetic acid (TFA). All the solvents used for this analysis were HPLC grade and obtained from Sigma-Aldrich (TFA) or Fischer Scientific (ACN).

Example IV

Mass Spectrometry

Samples were purified by RP-HPLC and appropriate amounts were taken in 50% acetonitrile solution containing 1% formic acid. They were analyzed in the positive ion mode using electro spray ionization technique on a Micromass ZMD quadrupole mass analyzer. The samples were introduced via a Harvard apparatus Pump 11 at a flow rate of 30 µl/min. The solvents used were of HPLC grade obtained from Fischer Scientific.

Example V

Light Microscopy

Samples of the reaction mixture (15 µl) were stained with 0.5 mM ethidium bromide and 10 µl aliquots were examined by standard phase contrast and fluorescence microscopy methods at 400× magnification. To determine the extent to which hydrolysis of ester bonds in phospholipids could affect lipid bilayer stability, we also extracted phospholipids from the reaction mixture using equal volumes of 2:1 chloroform methanol. Aliquots of the chloroform phase (10 µl) were then dried on glass slides, rehydrated with 10 µl of water on a cover slip that then was allowed to settle over the dried lipid, and examined at 400× magnification by phase microscopy. This procedure was carried out after 1, 3, 5, and 7 cycles.

Example VI

Nanopore Analysis

A nanopore instrument was used for single molecule analysis of RNA samples. The detailed method is described in Akeson et al. (Akeson M, Branton D, Kasianowicz J J, Brandin E, Deamer D W (1999) Biophys J. 77: 3227-3233). Briefly, in the nanopore instrument, a U-shaped patch tube with a 30 µm diameter aperture is supported by a custom-made Teflon structure which contains two 90 µl wells connected through the patch tube. The wells were filled with 70 µl 1.0 M KCl-HEPES buffer, and a solution of diphytanoyl-sn-glycero-3-phosphocholine in hexadecane (25 mg/ml) was painted across the aperture to form a bilayer. Aliquots of α-hemolysin (10 µg/ml) were added to the cis side of the bilayer by pipetting and thoroughly mixed. Typically in 10-20 min a heptameric channel of hemolysin assembled and inserted into the bilayer, as detected by a steady 120 pA current at 120 mV applied potential. Samples to be analyzed were reconstituted in 14 µl of 1.0 M KCl/50 mM HEPES buffer, and applied to the cis side of the nanopore. When a linear polyanion such as single stranded RNA is captured by the electrical field in the pore, it is translocated through the pore by single molecule electrophoresis and its presence in the pore transiently blocks the ionic current. Translocation events were detected by an Axopatch 200B patch clamp amplifier and recorded using P-clamp 9.0 software. (Axon Instruments). Duration and amplitude were analyzed and plotted with Clampex and Clampfit software.

Example VII

Nanopore Analysis

We reasoned that yields would be low if RNA-like polymers long enough to have catalytic activity were synthesized from mononucleotides that were not chemically activated. We therefore used a nanopore instrument to analyze solutions in which polymerization may have taken place. Nanopore analysis can detect single linear polyanions such as RNA and DNA and therefore provides a highly sensitive method to scan solutions for products of a polymerization reaction (Kasianowicz et al. (1996) Proc. Natl. Acad. Sci. USA 93: 13770-13773; Akeson et al. 1999 supra; Howorka et al. (2001) Nat. Biotechnol. 19: 636-639; Meller and Branton (2002) Electrophoresis 23: 2583-2591; Deamer and Branton (2002) Accounts Chem. Res. 35: 817-825). As described in the "Methods" section, a commonly used nanopore is α-hemolysin, which self-assembles in a lipid bilayer into a heptamer containing a limiting aperture of 1.5 nm. The nucleic acid sample is then added to the cis compartment, and the electric field produced in the pore captures single-stranded nucleic acids that are translocated through the pore by electrophoresis. Each translocation event is detected as a characteristic blockade of the ionic current. The amplitude and duration of the blockade provide information about the composition and length of the nucleic acid strand. For instance, the length of polyadenylic acid homopolymers is directly related to the average duration of the polymer passage through the nanopore (Akeson et al. 1999, supra), with typical translocation times of ~18 µs/base.

The first indication of RNA synthesis from AMP in a lipid environment was the appearance of ionic current blockades detected by the nanopore instrument. FIG. 1 shows examples of blockades produced by known 50 mers of polyadenyclic acid compared with samples taken from a mixture of 5'-AMP and 1-palmitoyl-2-oleoylphosphatidylcholine (POPC) that had undergone seven hydration-dehydration cycles. Previous investigations (Akeson et al. 1999, supra) showed that individual polyadenylic acid molecules driven by electrophoresis through a nanopore blocked 85% of the ionic current through the pore. Translocation occurred at a rate of approximately 18-20 ?s/base, so that the blockade signal of a 50 mer would typically be ~1 ms in duration. Examples of a typical blockade and a less common longer blockade are shown on the left in FIG. 1, and compared with several blockade signals from a sample of 5'-AMP subjected to seven hydration-dehydration cycles in the presence of POPC. The blockades resembled those of polyadenylic acid 50 mers, but had a wider range of amplitude and duration due to the variable polymer length and chemical composition. In our experience such blockades can only be produced by linear polyanions such as single-stranded nucleic acids in the range of 20-100 mers. The fact that blockades were present was conclusive evidence that linear strands of an RNA-like polymer had been synthesized.

FIG. 1 illustrates nanopore analysis of RNA-like products. FIG. 1a show blockades produced by a known 50 mer of polyadenylic acid. Typical blockades range around 1 ms in duration, representing a translocational velocity of 20 µs/base to pass through the nanopore. The presence of the RNA in the pore blocks approximately 85% of the ionic current that passes through the open channel. A few blockades last as much as ten times longer, but still have the same amplitude. FIG. 1b illustrates blockades produced by the RNA-like product from AMP:POPC (4:1) after five cycles. The duration and amplitude of the blockades had a greater range than the known 50 mer because of variations in chain length and conformation.

Figure 2:
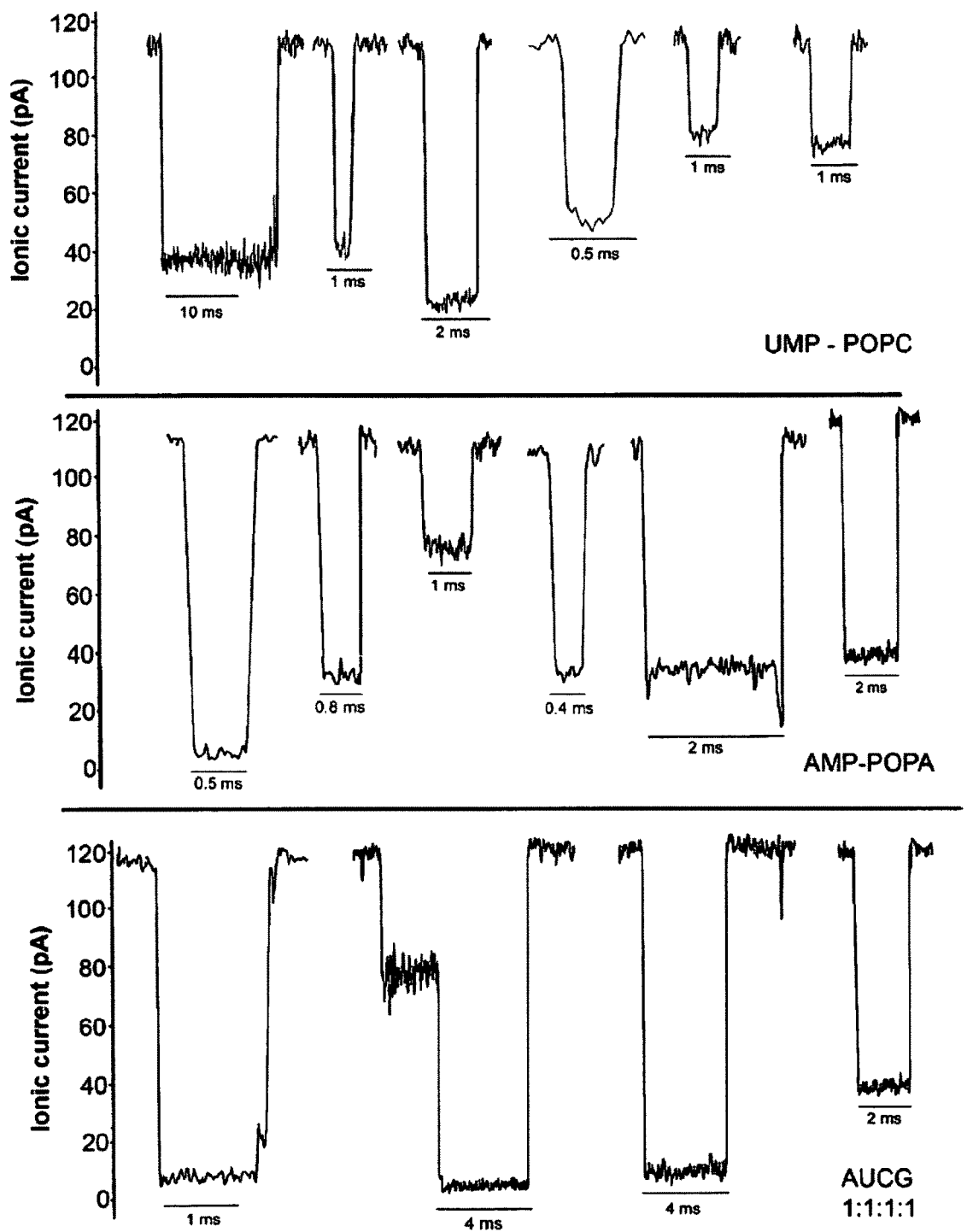
FIG. 2 shows examples of blockades produced by 5'-UMP: POPC, 5'-AMP:POPA, and by equimolar mixtures of all four nucleotides in 4:1 ratios with POPA.

FIG. 2 shows examples of blockades produced by 5'-UMP under the same conditions, by 5'-AMP in the presence of phosphatidic acid (POPA) and by an equimolar mixture of all four 5' nucleotides of RNA. These results indicate that the polymerization reaction is robust. Both purine and pyrimidine nucleotides can undergo polymerization, as can mixtures of all four nucleotides of RNA. Solutions of 5'-AMP alone (2.5 mM) did not produce blockades, nor did control experiments run in the absence of lipid (not shown).

FIG. 2 shows examples of blockades produced by 5'-UMP: POPC, 5'-AMP:POPA, and by equimolar mixtures of all four nucleotides in 4:1 ratios with POPA. UMP:POPC mixtures under the conditions of FIG. 1 tended to fall into two levels of blockade amplitude, and examples are shown here (top panel). Phosphatidic acid (POPA, center panel) was as effective as phosphatidylcholine (POPC) in promoting polymerization of 5'-AMP, and mixtures of all four nucleotides readily produced RNA-like molecules detected by their ionic current blockades (lower panel).

Figure 3:
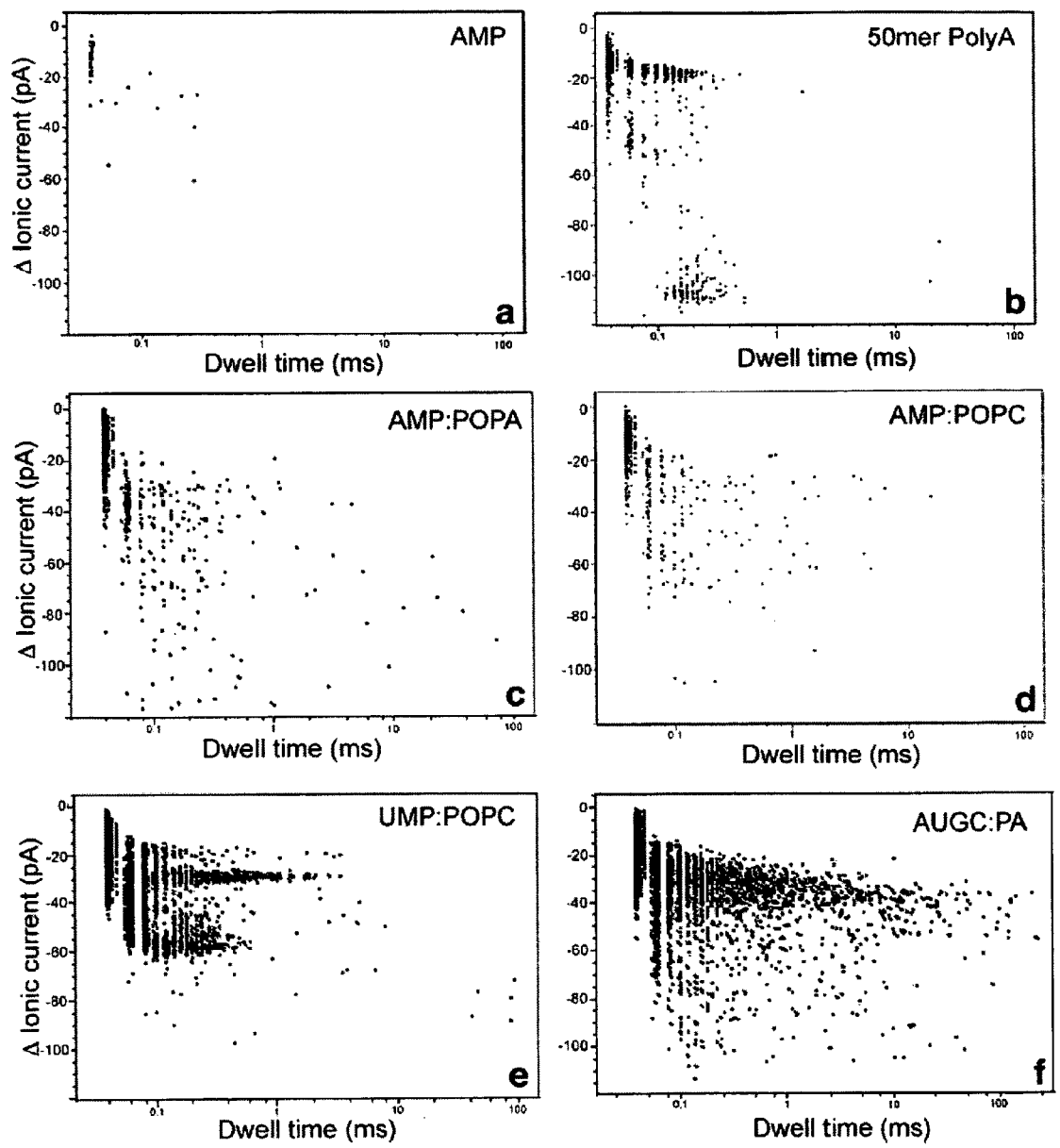
FIG. 3 shows event diagrams in which blockade amplitude in picoamps is plotted against blockade duration in milliseconds.

Although the presence of ionic current blockades provided qualitative evidence that RNA-like polymers were produced under the specified conditions in the presence of lipids, a more quantitative analytical approach is to plot blockade duration against amplitude of each blockades. Such plots are referred to as event diagrams, and provide statistical information about the results because hundreds of individual blockades can be compared as populations (FIG. 3). As noted earlier, no blockades are produced by AMP solutions by themselves (FIG. 3a). The few scattered events that are present near the origin are accounted for by electrical noise picked up by the instrument. FIG. 3b shows the signals produced by 10 µM polyadenylic acid 50 mers. Note that the majority of events are present in a group with an average duration of 1 ms and 20 pA residual current, representing a blockade amplitude of 85%. This result is in accordance with previously reported data (Akeson et al. 1999, supra). FIG. 3c shows the event diagram for the RNA-like oligomers synthesized from 5'-AMP in the presence of POPA after 7 hydration-dehydration cycles. As would be expected, the blockades are considerably more variable in amplitude and duration than the 50 mer. This is due to the fact that the blockades are produced by oligomers having a wide range of chain lengths, as well as variable secondary structures produced by a random distribution of 2'-5' and 3'-5' phosphodiester bonds. FIG. 3d-f show event diagrams for other combinations of nucleotides and lipids. It is interesting that the oligomers produced from UMP (FIG. 3e) separate into two groups in terms of blockade amplitude. This may be due to one species of oligomer only partially penetrating the nanopore, then falling out before full translocation has occurred.

FIG. 3 shows event diagrams in which blockade amplitude in picoamps is plotted against blockade duration in milliseconds. Each point represents the amplitude and duration of a single polymer molecule as it is translocated through the pore by an applied voltage of 120 mV. FIG. 3a shows an open channel current with no additions. A few short-lived low amplitude events seen in the control run are due to transient electronic noise. FIG. 3b shows blockades produced by a known 50 mer of polyadenylic acid. The group of events between 0.1 and 1 ms represent complete translocations of RNA through the nanopore. Short duration and low amplitude events are due to the RNA entering the pore but then diffusing away before translocation occurs (Akeson et al. 1999, supra). FIGS. 3c and 3d show blockades produced by AMP:POPA and AMP:POPC reaction products had a range of amplitudes and durations. This is because the blockades are produced by mixed oligomers ranging from the minimal length detectable by nanopores (5-10 mers) to as long as 100 mers. Because each oligomer has variable numbers of 2'-5' and 3'-5' phosphodiester bonds, the durations and amplitudes of the blockades will be considerably more varied than those of the polyadenyclic acid 50 mer that has a specified length and only 3'-5' bonds. FIG. 3e shows the event amplitudes produced by oligomers of 5'-UMP fall into two distinct groups having 25 and 50% blockades of ionic current. The reason is not yet understood. FIG. 3f shows that a mixture of all four nucleotides reacting in the presence of POPA had a robust yield of products. Some of the blockade durations were very long, with a substantial number over 10 ms. This is probably due to secondary structures in the oligomers which must be unravelled during translocation and therefore increase the event duration.

Example VIII

Yields of RNA-Like Polymer

Because the nanopore results indicated that small amounts of polymers were synthesized from mononucleotides in the presence of lipids, we were interested in determining yields, length of the polymers, and the nature of the chemical bonds linking the monomers. Yields of the RNA-like polymers were determined by performing RiboGreen assays (BioTek, Inc., Winooski, Vt.). This method was chosen as a general quantitative approach for two reasons. First, it is highly sensitive and gives useful estimates of nanogram to microgram quantities of RNA such as polyadenylic acid. (The assay is much less sensitive to polyuridylic acid, so it was applied here only to products from AMP polymerization.) The second reason is related to the complexity of the polymeric products. From previous work on clay-catalyzed polymerization reactions, we expected that products were likely to be composed of RNA-like molecules having a broad range of chain lengths and variable amounts of 2'-5' and 3'-5' phosphodiester bonds within each molecule.

The total product ranged from 24 to 155 µg depending on several experimental variables, (FIG. 4) with the higher amount equivalent to ~6% yield of polymers by weight. Yields generally increased with the number of cycles the sample had experienced, typically reaching an apparent plateau after five cycles. Yields were highest when 1-palmitoyl-2-oleoylphosphatidic acid (POPA) was used (FIG. 2a), followed by lysophosphatidylcholine (LPC) and 1-palmitoyl-2-oleoylphosphatidylcholine (POPC). The yield obtained at 90° C. was significantly greater than at 60 and 70° C. (FIG. 2b). Base-catalyzed hydrolysis (0.1 M NaOH, 10 min, 60° C.) entirely hydrolyzed the RNA-like polymer to its component monomers as indicated by thin layer chromatography (not shown). This result excludes the possibility that bonds other than ester bonds were involved in the polymerization reaction.

Figure 4:
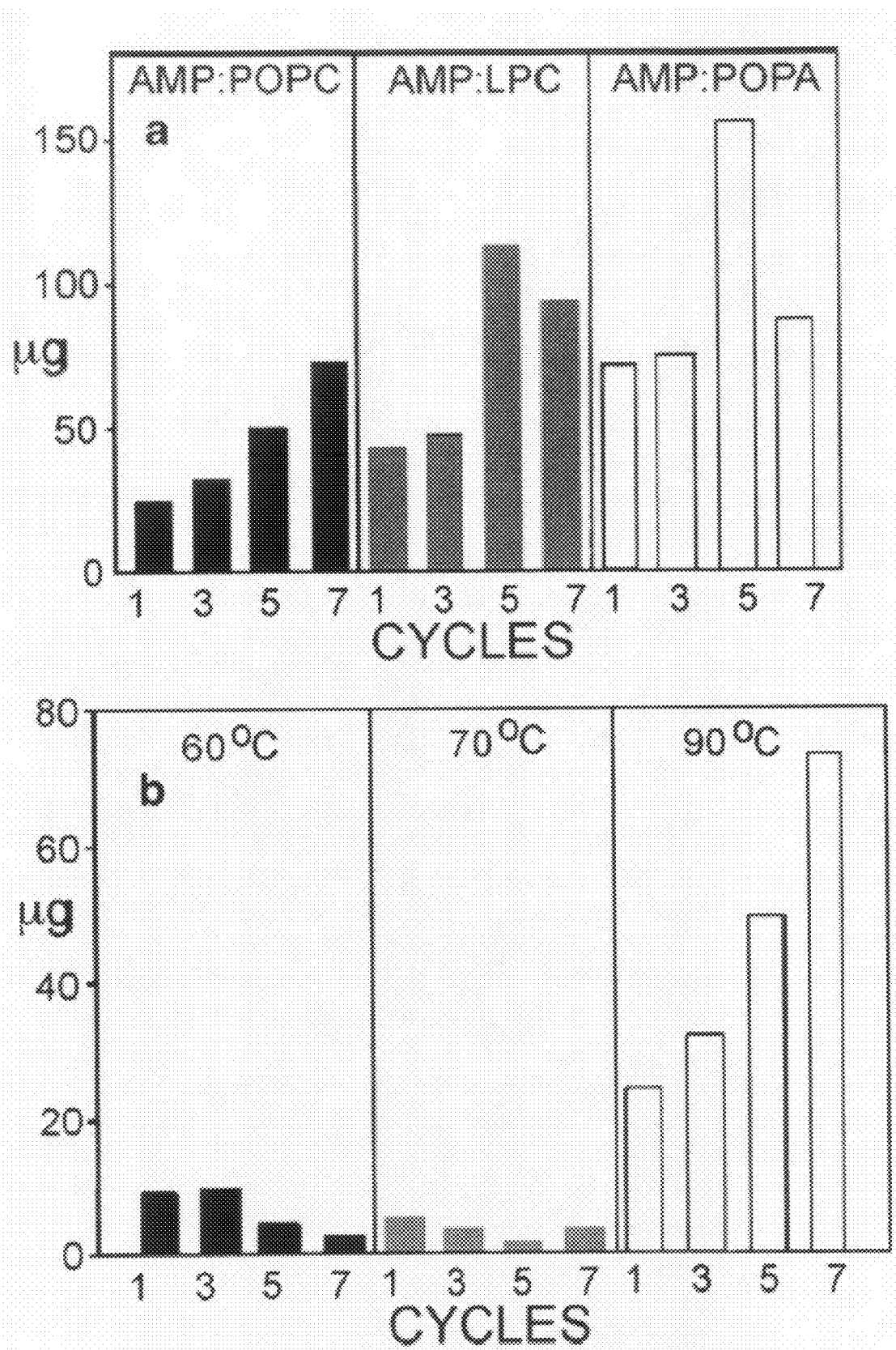
FIG. 4 illustrates yields of RNA-like polymers obtained under different conditions.

FIG. 4 shows yields of RNA-like polymers obtained under different conditions. Experimental variables included the number of cycles and species of lipid (a), and temperature (b). In FIG. 4a, the monocleotide to lipid ratios were 2:1 (POPC), 1:1 (LPC) and 2:1 (POPA). In FIG. 4b the AMP to lipid ratio was 2:1. All reactions were carried out at 90° C.

Example IX

Gel Patterns of RNA-Like Products

The results from nanopore analysis and RiboGreen assays were consistent with the possibility that linear strands of RNA-like polymers were synthesized in the presence of lipid. In order to confirm these observations and to determine the length of possible polymers, we used a procedure that produces radioactively labeled products for analysis by gel electrophoresis. The products were first treated with alkaline phosphatase to remove phosphate at the 5' end, then labeled with γ-[$^{32}$P]ATP using T4 polynucleotide kinase and analyzed by denaturing polyacrylamide gel electrophoresis.

This experiment was run multiple times using a variety of controls and conditions, including the number of cycles, species of lipid and nucleotide, nucleotide-to-lipid ratio and temperature. FIG. 5a shows one such series in which the number of cycles was varied, using AMP and POPC in a 2:1 mole ratio. The amount of labelled RNA-like polymers increased steadily over seven cycles, which was consistent with the indications of the RiboGreen assay (FIG. 5a). Most of the RNA-like polymers ranged from 25 to 75 nucleotides in length, with a smaller fraction in the 100 mer range. This range of chain length was apparent even after a single cycle, and subsequent cycles served to increase the amount of polymer, but not the chain length. The labeled polymers shown in the gels consist of longer chains that were precipitated in ethanol, representing only a fraction of the total nucleotides initially present. The remainder, together with oligonucleotides shorter than 10 mers, was removed at this step in the procedure.

Figure 5:
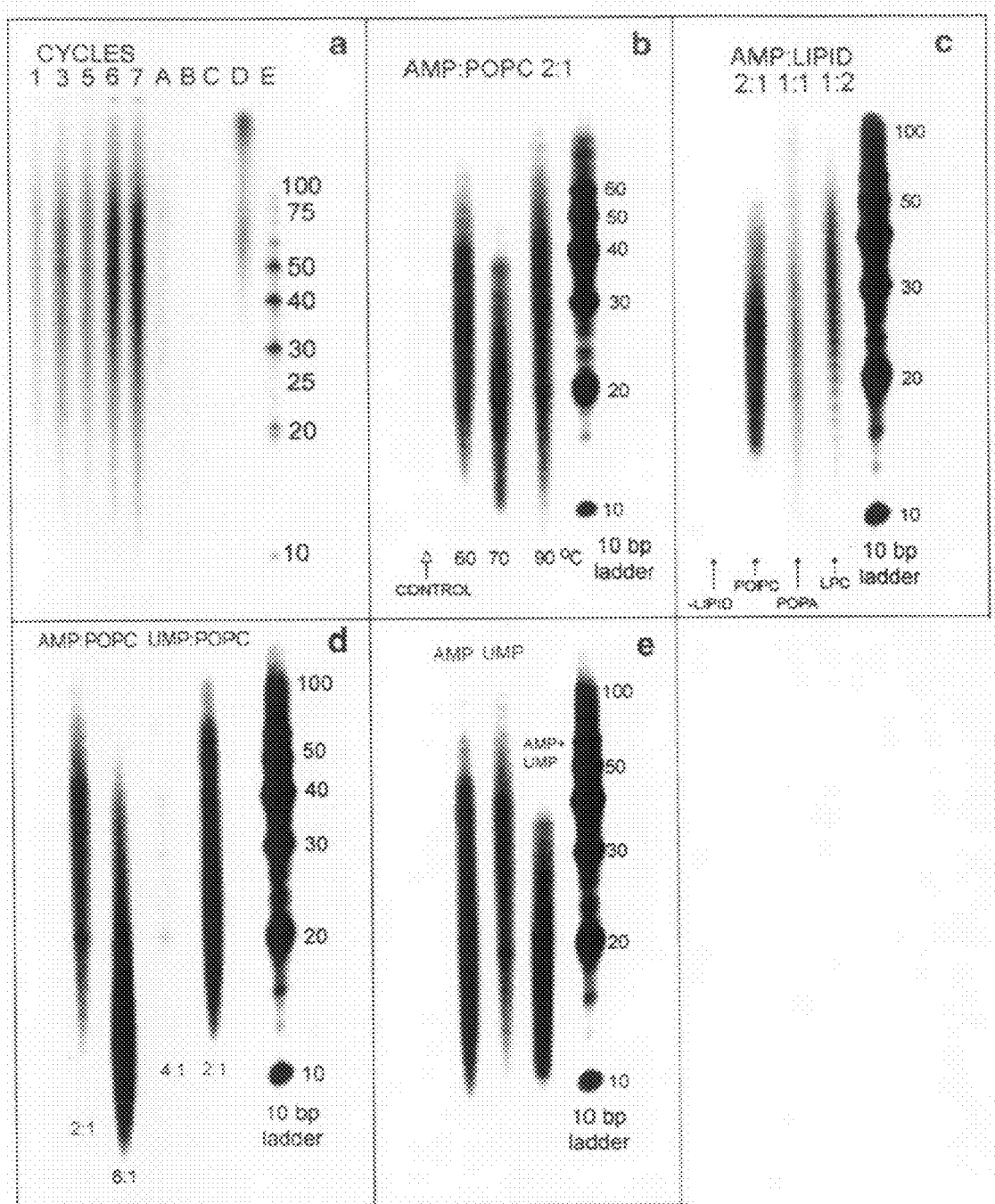
FIG. 5 shows the gel patterns of RNA-like products end-labeled with AT$^{32}$P.

FIG. 5 shows the gel patterns of RNA-like products end-labeled with AT$^{32}$P. a shows the result of varying the number of cycles from 1 to 7. The reaction conditions were AMP: POPC 2:1. Several controls are also shown. Lane A: air was used instead of carbon dioxide during drying (7 cycles). Lane B: Lipid absent (7 cycles). Lane C: unheated control. Lane D: 10 µg of commercial polyadenylic acid as a positive control for the end labeling process. Lane E shows an RNA ladder containing known lengths of RNA in 10 nucleotide (nt) increments. The effects of varying temperature (b), lipid (c), mononucleotide to lipid ratio (d), and mixtures of mononucleotides (e) were also investigated. (See text for details.) The abbreviations for lipid are POPC (1-palmitoyl-2-oleoylphosphatidylcholine) POPA (1-palmitoyl-2-oleoylphosphatidic acid) and LPC (egg lysophosphatidylcholine). The abbreviations for mononucleotide (AMP, 5'-adenosine monophosphate; UMP, 5'-uridine monophosphate) also indicate which lipid was used and the mole ratio of mononucleotide to lipid.

A series of controls is shown in the lanes labeled A-D. If air was used instead of carbon dioxide in seven drying cycles, much less labeled polymer was observed (lane A). However, carbon dioxide and nitrogen atmospheres gave similar yields, so perhaps atmospheric oxygen in some way partially inhibits the reaction. If the experiment was run for seven cycles in the absence of lipid (lane B) or if cycling was not carried out (lane C) yields of labeled product were undetectable. Commercial polyadenylic acid was run as a positive control (lane D).

FIGS. 5b-f show the effect of several experimental variables on the lipid-dependent RNA-like polymer synthesis reaction, which included temperature, substitution of different lipid and nucleotide species, and mixtures of nucleotides. Products were detected by end-labeling for all three temperature ranges tested (FIG. 5b) with the highest yields at 90° C. All three lipids promoted the condensation reaction (FIG. 5c) but products were much reduced in the absence of lipid. The nucleotide to lipid ratio affected both chain length and apparent yield (FIG. 5d). Substituting UMP for AMP seemed to have little effect on the yield of polymer (FIG. 5e) but the resulting chain lengths were markedly reduced in a 1:1 mixture of AMP and UMP, perhaps because the mixed purine and pyrimidine nucleotides are less stabilized by stacking energy than the pure nucleotides.

These results, taken together with the nanopore and electrophoresis results, confirmed that linear RNA-like polymers were the primary product of the reaction. Although we are confident that linear polymers are synthesized in the presence of lipid, it should be noted that the experimental conditions are much more complex than those of a typical chemical reaction. Each lane of reaction products shown in FIG. 5 represents a separate experiment, and during each wet-dry cycle there is a remixing of lipid, polymeric products and mononucleotide reactants. The reaction does not occur in solution, but instead in the interlamellar space of lipid lamellae (multilayer phospholipids) in the dried film. This complexity could lead to considerable variation of yield from one sample to the next, and also to variation in the chemical nature of the phosphodiester bonds (both 2'-5' and 3'-5' bonds are present) and the 5'-ends of the RNA.

Example X

HPLC and Mass Spectrometry

HPLC and mass spectrometry are commonly used to analyze oligomeric RNA (Ferris (2002) Orig. Life Evol. Biosphere 32: 311-332). However, for several reasons the oligomeric products reported here are less amenable to such analytical techniques. They have a range of lengths, as shown in the gel patterns above, and variable conformations due to random mixtures of 2'-5' and 3'-5' bonds. Furthermore, the only oligomers observed in gels were those with end groups that could be recognized by the two enzymes required for end labelling. Substantial amounts of oligomers with other end groups are likely to be present, such as cyclic phosphodiester bonds and even cyclic oligomers, rather than linear chains. We did carry out preliminary HPLC analysis, and could observe small amounts of products ranging up to 10 mers. Longer oligomers were either too low in concentration or too variable in composition to be separated and observed by HPLC as distinct peaks. Preliminary mass data indicated the presence of oligomers in the 20-30 mer range. A full analysis by HPLC and mass spectrometry will require large-scale preparations in order to yield oligomers in amounts sufficient to undergo further purification.

Example XI

Microscopic Appearance and Lipid Stability

Figure 6:
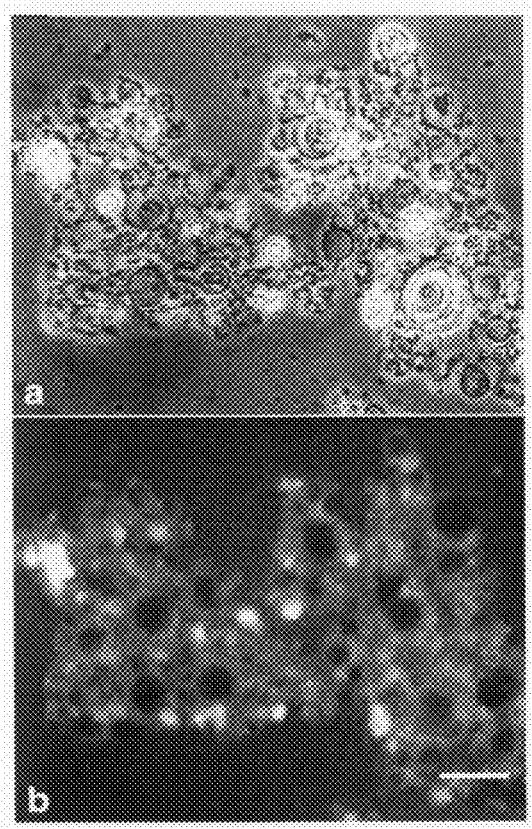
FIG. 6 shows the microscopic appearance of lipid structures after seven cycles visualized by phase (a) and fluorescence (b) microscopy. Reaction conditions were AMP:POPC 2:1. Bar shows 20 mm.

Membranous vesicles could be observed following rehydration after seven cycles of dehydration and heating at 90° C. A phase micrograph of such vesicles is shown in FIG. 6a. The fact that vesicles are visible demonstrates that fusion has occurred during the drying cycles, because the original vesicles were in the sub-micron size range and would not be resolved by phase microscopy. The same preparation was stained with 0.1 mM ethidium bromide, which intercalates into RNA structures and produces a fluorescent stain if RNA is present. FIG. 6b shows a fluorescence image of the same sample. A diffuse fluorescence was pervasive, but some vesicles showed unstained interior volumes while others were brightly fluorescent. The presence of unstained vesicles lacking encapsulated material is predicted from the vesicle fusion that occurs during dehydration, because solutes are excluded from lamellar layers that were originally the interior of the lipid vesicles (Deamer and Barchfeld 1982, supra). We cannot be certain of the nature of the vesicles with higher content of fluorescently stained substances, but if long strands of RNA-like molecules are in fact present, it is possible that some of the products may accumulate in aggregates, rather than being dispersed throughout the lipid phase. Similar aggregates could be seen in control preparations in which phosphatidylcholine vesicles were dried and rehydrated in the presence of biological RNA. Ethidium bromide staining produced no initial fluorescence in control lipid samples that were dried and then rehydrated in the absence of RNA (not shown).

We noticed in the micrographs that POPA vesicles, after several cycles, were somewhat disordered and aggregated, suggesting that partial degradation of the lipid was occurring. For this reason we followed the lipid composition by thin layer chromatography on silicic acid plates. The patterns clearly showed that after five cycles a significant fraction of POPA had hydrolyzed to lysophosphatidic acid and fatty acids, which appeared as separate spots on the plate. This was not the case with LPC and POPC vesicles that were significantly more stable to the wetting and drying cycles.

Figure 7:
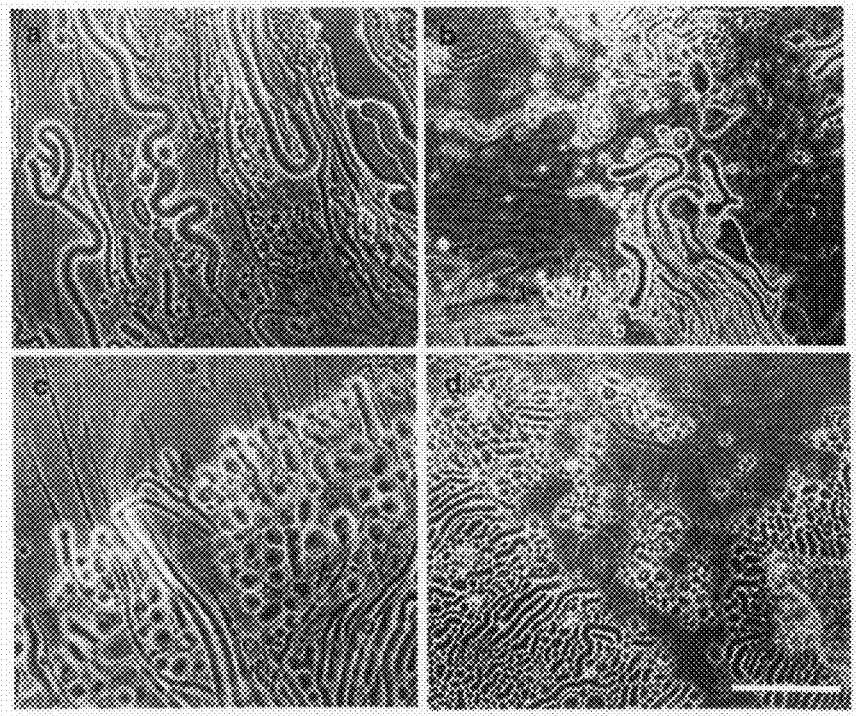
FIG. 7 illustrates the effect of cycling on integrity of phosphatidylcholine. Lipid was extracted from samples that had undergone 1, 3, 5, and 7 cycles of dehydration-rehydration (FIGS. 7a, 7b, 7c, and 7d, respectively).
Figure 8:
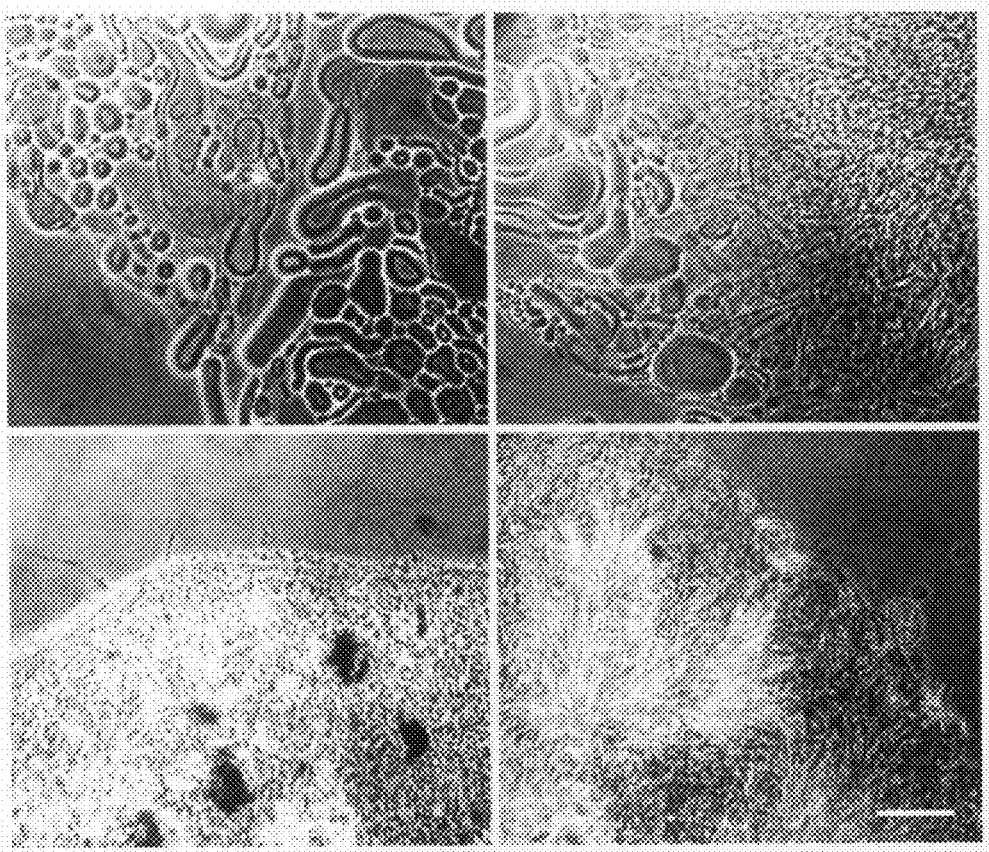
FIG. 8 illustrates the effect of cycling on integrity of phosphatidic acid (POPA).
Figure 9:
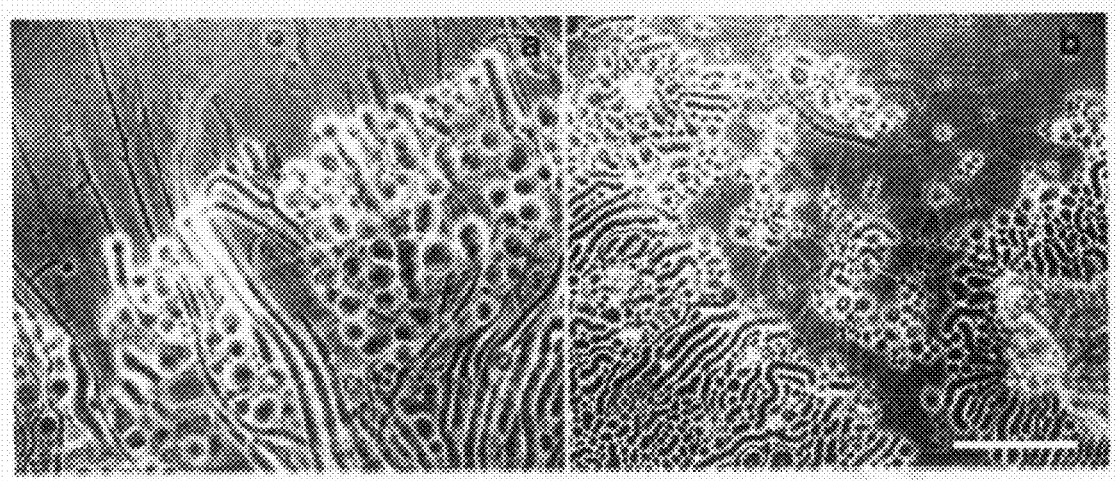
FIG. 9 illustrates the effect of cycling on integrity of lyso-phosphatidylcholine (LPC).

We also carried out microscopic examination of self-assembled lipid structures that form when dried lipid extracts are rehydrated following several cycles thereby creating an ordering microenvironment (FIGS. 7, 8, and 9). All of the lipids produced typical myelin figures and vesicles after one cycle of dehydration and heating, but after five cycles the hydrolysis occurring in phosphatidic acid samples was clearly affecting the self-assembly process. Bulk-phase crystals of fatty acid hydrolysis products (a mixture of palmitic and oleic acid) began to appear in the POPA samples following rehydration, while POPC and LPC were apparently unaffected. All three lipids were able to promote polymer synthesis (see FIG. 4a), so acid-catalyzed hydrolysis of the lipid does not seem to be a limiting factor in the reactions leading to polymer synthesis, at least after five cycles. The decreased yield observed after seven cycles in the presence of POPA (FIG. 4a) may be due to extensive hydrolysis of the phosphatidic acid to fatty acids. These do not form lamellar arrays of bimolecular membranes, and therefore are less able to promote the net synthesis of RNA-like polymers. Instead, the polymers present begin to undergo hydrolysis so that yields are reduced.

FIG. 7 illustrates the effect of cycling on integrity of phosphatidylcholine. Lipid was extracted from samples that had undergone 1, 3, 5, and 7 cycles of dehydration-rehydration (a-d in the panel). An aliquot of the extract (10 µl) was dried on a microscope slide and allowed to self-assemble into membranous structures. It is clear that POPC maintained its ability to produce lipid bilayer structures, represented in the images as multilamellar tubular myelin figures (multilayer phospholipids) and vesicles. Phase microscopy, 400× original magnification. Bar shows 20 µm.

FIG. 8 illustrates the effect of cycling on integrity of phosphatidic acid (POPA). In contrast to phosphatidylcholine, POPA began to undergo hydrolysis after 3 cycles (top right), and the reaction products—palmitic and oleic acid, and lysophosphatidic acid—began to form brushlike crystalline structures rather than membranes. These are clearly apparent after 5 and 7 cycles (lower panels). Phase microscopy, 400× original magnification. Bar shows 20 µm.

FIG. 9 illustrates the effect of cycling on integrity of lysophosphatidylcholine (LPC). This lipid, which has only one fatty acid on the 3-carbon, is relatively stable to hydrolysis. At low concentrations (<10 mM) LPC exists as micelles, but at the much higher concentrations of hydration from a dry phase it readily assembled into bilayer structures after one cycle (a) as well as after seven cycles (b) Phase microscopy, 400× original magnification. Bar shows 20 µm.

Example XII

Synthesis of dsDNA Using a ssDNA Template

We chose to use phosphatidic acid, because it is the simplest phospholipid, consisting of a glycerol phosphate linked to two fatty acids through ester bonds. 1-Palmitoyl-2-oleoyl-sn-glycero-3-phosphate (POPA) was purchased from Avanti Polar Lipids Inc (Alabaster, Ala., USA). dNMPs (Thymidine 5-monophosphate disodium salt hydrate 99%, 2-Deoxyguanosine 5-monophosphate sodium salt hydrate 98-100%, 2'-Deoxycytidine 5'-monophosphate Sigma Grade, 98-100%, and 2-Deoxyadenosine 5-monophosphate sodium salt Sigma Grade, 96%) and PEG (15000-20000 Da) were from Sigma Aldrich Company Incorporated (St. Louis, Mo., USA). The DNA template was purchased from Integrated DNA Technologies, Inc. (Coralville, Iowa, USA) and had the following sequence: 5'-CCC CCC GCC TCC TCC GCC ACC ACC GCC TCC TCC TCC TCC GCC TCC TCC GCC AAA AAA AAA AAA A-3' (SEQ ID NO: 2), which was designed to have minimal potential for secondary structure. SYBR GREEN I gel stain, which is specific marker of dsDNA, and QUANT-IT PICOGREEN dsDNA Assay Kit were purchased from Molecular Probes (Eugene, Oreg., USA). The 50 bp dsDNA ladder, FauI restriction enzyme and its NEB 1 reaction buffer (10 mM Bis-Tris-Propane-HCl, 10 mM $MgCl_2$, 1 mM Dithiothreitol, pH 7.0 at 25° C.) were from New England Biolabs (Ipswich, Mass., USA). HCl, butyl alcohol, $NH_4OAc$, and $MgCl_2$ were from Fisher Scientific Company LLC (Santa Clara, Calif., USA). Hexane (HPLC grade) was from Honeywell International Inc. Burdick & Jackson (Muskegon, Mich., USA). The water was purified using a Milli-Q Synthesis System from Millipore (Molsheim Cedex, France) and the ethanol was from Gold Shield Distributors (Hayward, Calif., USA).

Example XIII

Abiotic Reaction and Nucleic Acid Purification

The reaction vessels were 10 ml glass test tubes fitted with synthetic latex stoppers. Each stopper had and inlet for gas flow, a second inlet through which water could be injected from a syringe, and an outlet for gas that passed over the reaction. A preparation of 5 mg/ml POPA and equal amounts of dTMP, dGMP, dCMP and dAMP at a total nucleotide concentration of 20 mg/ml were mixed in 0.5 ml MilliQ $H_2O$. Template oligomer (5 µg) was added and the mixture was incubated at 90° C. for 2 hours under a continuous gentle stream of $CO_2$ gas that served to remove water as it evaporated from the mixture. After rehydrating the reaction mixture for 10 minutes with 0.5 ml of HCl (1 mM), the incubation was repeated. A low pH range (approximately pH 3) was used to protonate the template and nucleotides in order to promote complementary base pairing and condensation reactions in which water molecules became leaving groups. This incubation-rehydration cycle was repeated 5 times and 0.5 ml MilliQ $H_2O$ was used for the last rehydration. Two volumes of n-butanol were mixed to extract the lipid and then removed by vacuum suction through a glass Pasteur pipet. After two extractions, the remaining butanol was removed by repeating the same process with hexane. The product DNA, which was expected to be dsDNA composed of template and replicated strand, was isolated by addition of one volume of $NH_4OAc$ 4 M and 0.4 volumes of polyethylene glycol (PEG; 0.4 mg/ml, 1.6 M NaCl). Finally, 2 volumes of ethanol were added and the mixture was refrigerated at −20° C. for at least 4 days in order to precipitate the reaction product. To recover the nucleic acid, the solutions were centrifuged at 10,000 rpm for 30 min, ethanol was aspirated and the pellet was dried in air.

Example XIV

Detection of dsDNA Product by Fluorescence

The precipitate was resuspended in 0.5 ml TE buffer (10 mM Tris-HCl, 1 mM EDTA, pH 7.5) prepared from the concentrated stock provided in the QUANT-IT PICOGREEN dsDNA Assay Kit. The samples were incubated for a minimum of 30 minutes at room temperature to allow the product to bind with the template oligomer. Following manufacturer's instructions, the PICOGREEN fluorescent probe was diluted in TE buffer and 0.5 ml of this solution was added to each sample and standard solution (standards had the X-DNA provided in the kit). After a 5-minute incubation, the fluorescence was measured in a SLM 8000 spectrofluorimeter (SLM Instruments Inc., Urbana, Ill., USA).

Example XV

Atomic Force Microscopy

It was possible that a dsDNA product, if present, could be distinguished from the ssDNA template by AFM. After ethanol precipitation, the precipitate was resuspended in 10 μl $MgCl_2$ 5 mM and incubated as described above. 3 μl of this solution was spread on freshly cleaved mica, incubated at room temperature for 4 minutes, then rinsed with milliQ $H_2O$. The samples were dried initially under a $N_2$ stream and then kept under vacuum for 68.4 hours. AFM imaging was performed in tapping mode with a NANOSCOPE RIIIa (Digital Instruments, Santa Barbara, Calif.). The images were flattened in order to remove the background and particle size and distrubution were analyzed using the NanoScope software.

Example XVI

Gel Electrophoresis

We expected that a dsDNA produced by replication of a ssDNA template 64 nucleotides in length would appear as a 64 mer dsDNA on a gel. Precipitated samples were resuspended in milliQ $H_2O$, purified in Micro Bio-Spin P-6 columns from Bio-Rad Laboratories (Hercules, Calif., USA), loaded into a 20% acrylamide gel and run according to Chory and Pollard (Chory and Pollard (2001) Curr. Protoc. Mol. Biol. Chapter 2: Unit 2.7). A 50 bp dsDNA ladder was used as a size marker. The gel was post-stained using the dsDNA specific SYBRGREEN I fluorescent probe according to instructions provided by the manufacturer and scanned in a TYPHOON TRIO Variable Mode Imager (Amersham Biosciences Corporation, Piscataway, N.J.).

Example XVII

Restriction Enzyme Assay

Hydrolysis by a restriction enzyme was used to estimate the overall accuracy of replication, because a dsDNA product was expected to contain a sequence that could be targeted by the FauI enzyme. In a second experiment, samples were produced using twice the mass of reactants indicated above and purified as described in Methods. For the enzyme digestion, 5 units of FauI were used in NEB1 reaction buffer. The mixture was incubated at 37° C. for two hours. After the reaction, samples were analyzed by PAGE as indicated above.

Example XVIII

Yields of dsDNA

If ssDNA from the reaction mixture acted as a template for the synthesis of complementary DNA, we expected that dsDNA would be present in the reaction mixtures after the drying/rehydration cycles. In order to test if this reaction occurred, a dsDNA-specific fluorescent probe was added to the aliquots of the solution, as well as to a series of control samples. The results are presented in FIG. 10 and FIG. 11, and which compare fluorescence in solution with fluorescent bands in a gel.

Figure 10:
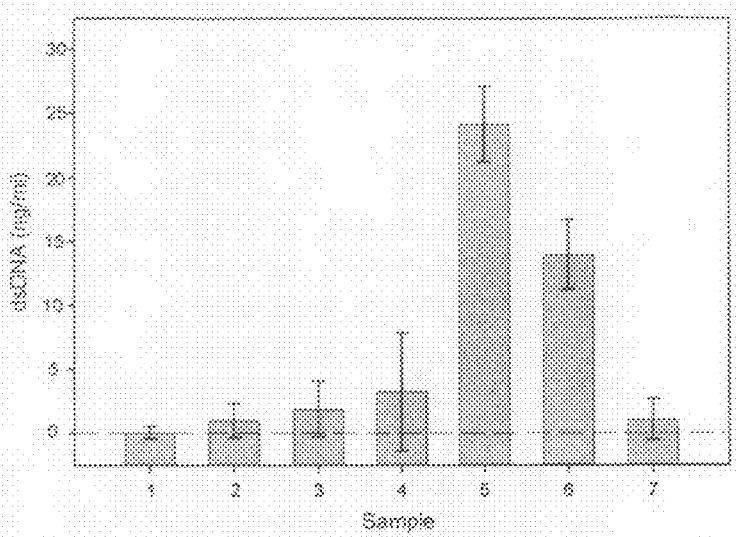
FIG. 10 shows exemplary solution fluorescence measurements.

FIG. 10 illustrates solution fluorescence measurements. 1) Mixture of dAMP, dCMP, dTMP and dGMP alone (sample 1); 2) Association of dNMPs to the template (sample 2); 3) Abiotic product in the absence of a template (sample 3); 4) Non-specific pairing of the abiotic product to the template (sample 4); 5) Specific pairing of the abiotic product to the template (sample 5); 6) Specific pairing of the abiotic product (produced in the absence of lipid) to the template (sample 6); 7) Association of dNMPs to the template, no lipid (sample 7). See Table 1 and text for details on the preparation of the samples.

TABLE 1

Summary of the experiment and controls

| Sample # | NSample preparation | | | | | Effect under study |
|---|---|---|---|---|---|---|
| 1 | + | − | − | − | − | dNMPs alone |
| 2 | + | + | − | − | + | Association of dNMPs to the template |
| 3 | + | + | + | − | − | Abiotic product in the absence of a template |
| 4 | + | + | + | − | + | Non-specific pairing of the abiotic product to the template |
| 5 | + | + | + | + | + | Specific pairing of the abiotic product to the template |
| 6 | + | − | + | + | + | Specific pairing of the abiotic product (produced in the absence of lipid) to the template |
| 7 | + | − | − | − | + | Association of dNMPs to the template, no lipid |
|  | Mixture of the four dNMPs | POPA | Heat cycling | Template during heat cycling | Template during analytical measurements | |

Figure 11:
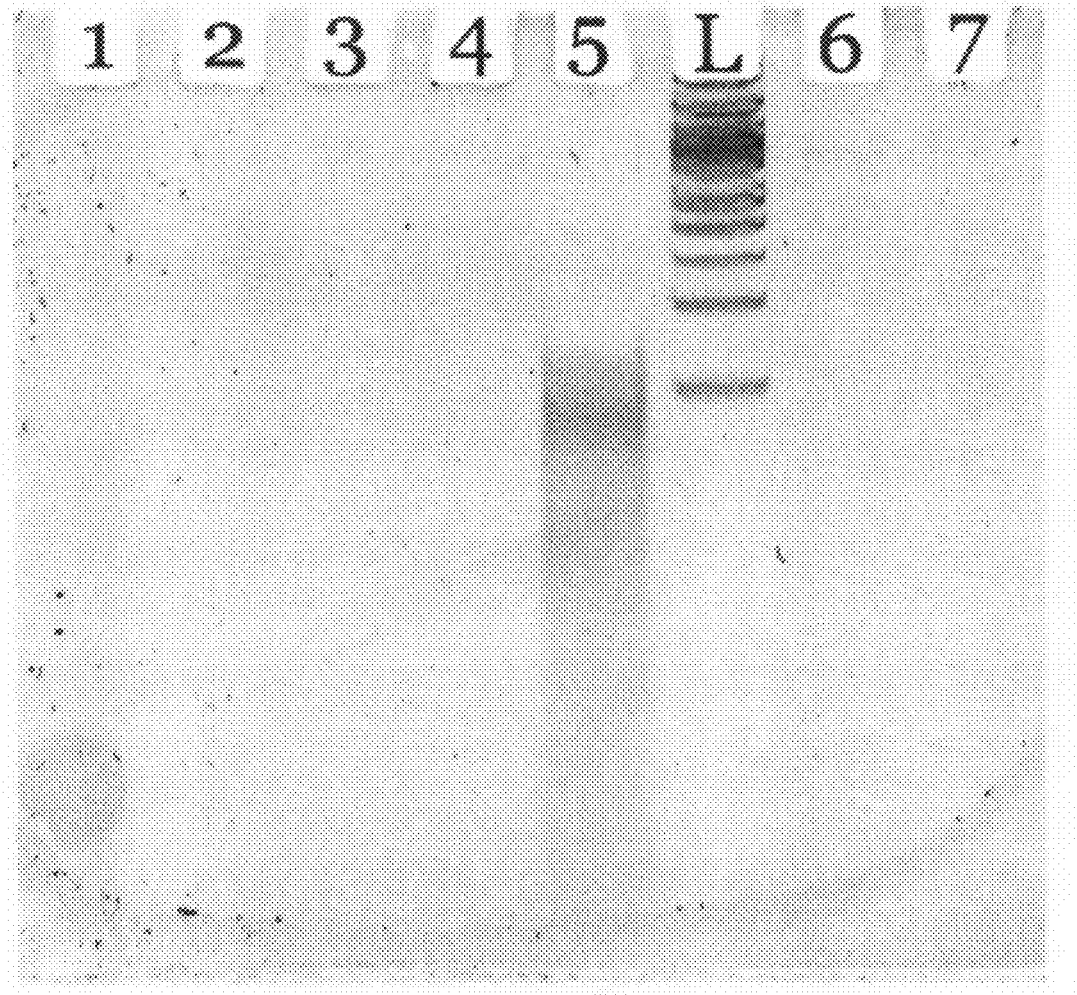
FIG. 11 shows an exemplary gel electrophoresis of dsDNA

FIG. 11 shows a gel electrophoresis analysis of the products. Lanes are numbered according to the sample they contain (Table 1). Lane L contains a 50 bp dsDNA ladder used as a size marker and as a positive control for the Sybrgreen I fluorescent probe staining.

Sample 5 had a significant fluorescence signal equivalent to 25 ng per ml, and the same sample in the gel showed a band at approximately the position expected of a 64 mer. Since molecules other than dsDNA can affect the fluorescence of the probes, a set of controls was prepared as shown in table 1 (the same numbers were used to designate samples throughout this section). One possibility is that the high concentration of dNMPs used in this experiment could cause a false positive that could be confused with dsDNA. Sample 1 controls for this possibility, and no excess fluorescent signal was observed for mixtures of the dNMPs alone of in the gel. Even if the dNMPs did not produce a measurable fluorescent signal, the high concentration at which they were present could promote association with the template to give a false positive. Also, even though the sequence of the template was chosen to minimize secondary structures as tested by mfold, it could still present some minimal structure that would again produce a false positive. However, sample 2 controls for this possibility, which showed low fluorescence in solution and no detectable band in the gel.

It was also possible that a measurable amount of dsDNA was produced without the addition of a template nucleic acid. For instance, polymers that formed could act as templates and promote the synthesis of complementary strands. Sample 3 discounts this possibility: the amount of fluorescence present in a sample lacking template was negligible, and there were no apparent bands in the gel. This observation is consistent with the low yields of the reaction. Even if new product could act as a template for further synthesis of complementary polymers, the low yield of replication (0.5% with respect to the template), together with the low yield of the reaction by itself (a maximum of 6% was achieved as disclosed above) leaves this effect outside the resolution limit. It is also possible that non-specific pairing of the abiotic product to the template would interfere with our measurements. This effect is accounted for in sample 4, which does not present a significantly higher fluorescence than the product of the reaction mixture in the absence of the template (sample 3).

Finally, the effect of the lipid on the reaction was addressed. A higher fluorescent signal was found in sample 5, containing lipid, than in sample 6, where it was absent. Even if small amounts of dsDNA were synthesized in the absence of lipid, the amount was not sufficient to produce a band in the gel. This observation and the results from sample 3 are consistent with the requirement of lipid for the synthesis of a detectable amount of dsDNA.

Sample 7 was prepared to determine whether the solution fluorescence in sample 6 was due to the association of monomers with the template, or perhaps that unextracted lipid produced a false positive. Sample 2 and sample 7 were prepared in a similar way, except for the lipid, which was added only to sample 2. Both samples presented similar fluorescence signals, showing that the extraction process was sufficient to remove most of the lipid.

Example XIX

Atomic Force Microscopy

Figure 12:
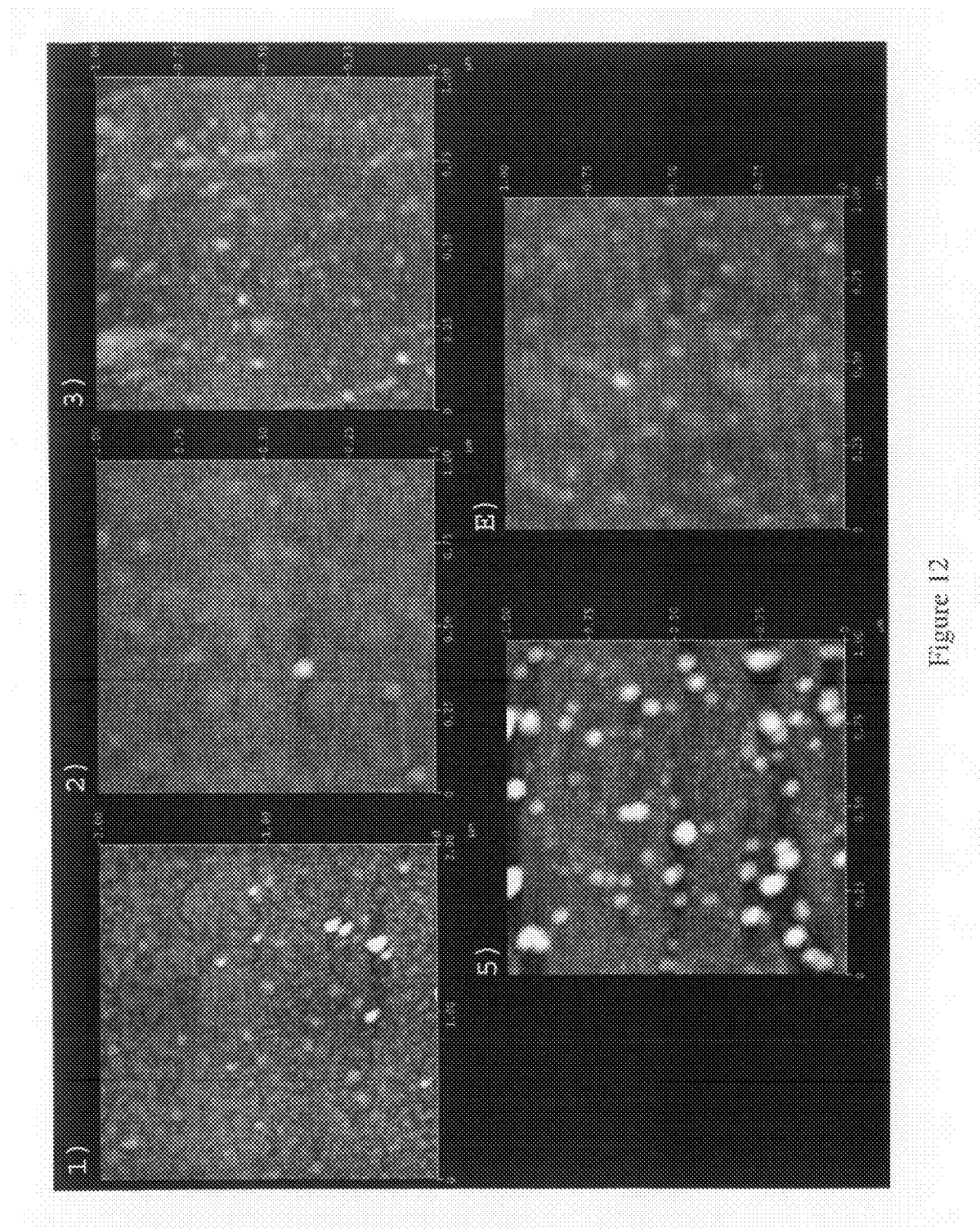
FIG. 12 illustrates atomic force microscopy (AFM) images.
Figure 13:
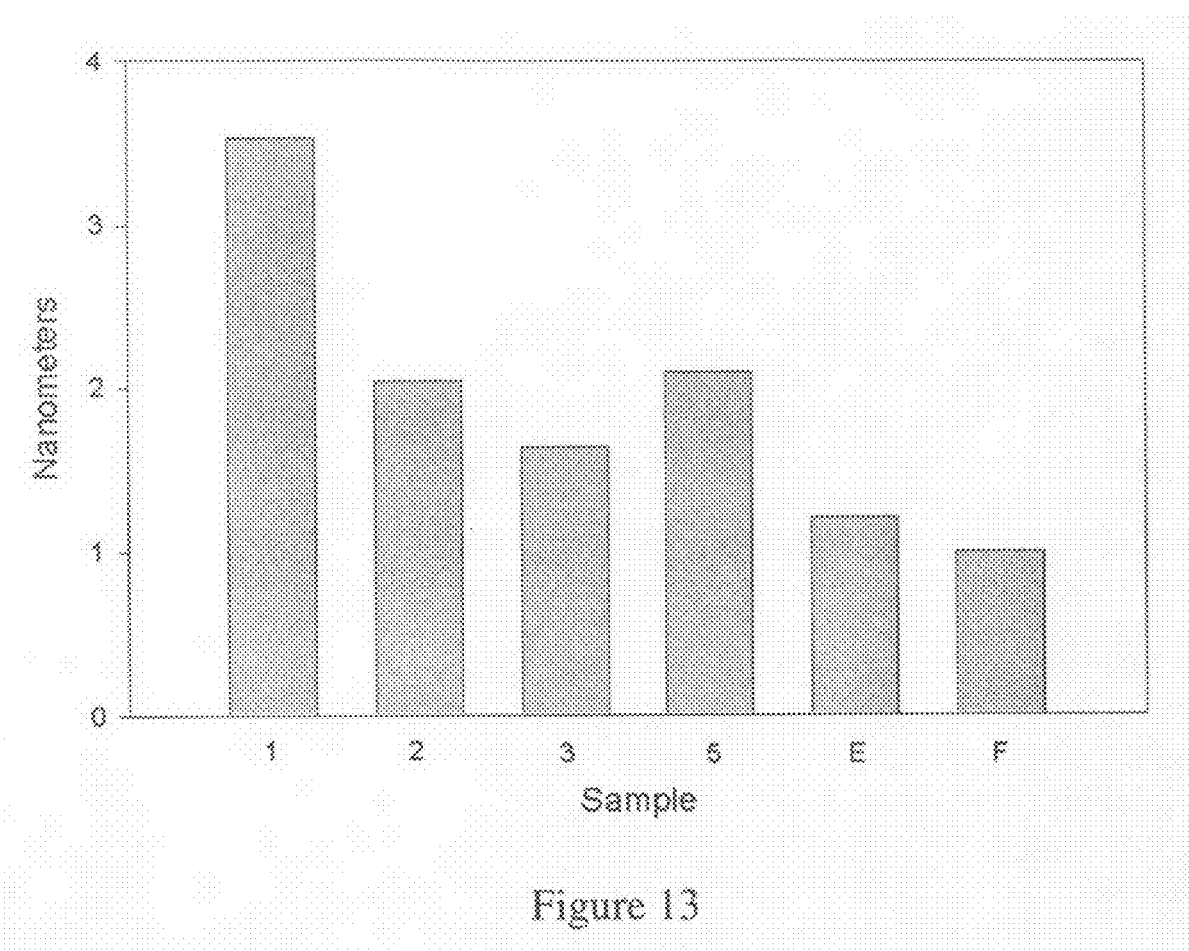
FIG. 13 shows an exemplary maximum height of particles measured by AFM.

The product from the condensation reaction was further studied by atomic force microscopy (AFM). Previous studies of ssDNA and dsDNA of a size range similar to that used here led us to expect that dsDNA, if present, would produce larger structures than the template ssDNA (Hansma and Laney (1996) Biophys. J. 70(4): 1933-1939). The template used for the reaction showed relatively homogeneous fields of globular structures (FIG. 12E). The product of the condensation reaction in the presence of template (sample 5) also showed mainly globular conformations (FIG. 12.5) but about twice as high. Although the appearance of sample 5 was clearly distinguishable from the controls, FIG. 13 shows that the heights of samples 2, 3 and 5 are comparable to the controls. This effect could be the result of structures including mononucleotide aggregates that form under the imaging conditions and it makes difficult to establish using AFM whether any dsDNA is present in the reaction product.

FIG. 12 shows AFM Images. 1) Mixture of dAMP, dCMP, dTMP and dGMP (sample 1); 2) Mixture of template and unreacted mononucleotides (sample 2); 3) Product of the abiotic reaction in the absence of template (sample 3); 5) Product of the abiotic reaction in the presence of template (sample 5); E) 64 mer oligomer DNA used as a template.

FIG. 13 shows maximum height of particles measured by AFM. 1) Mixture of dAMP, dCMP, dTMP and dGMP alone (sample 1); 2 Mixture of template and unreacted mononucleotides (sample 2); 3) Product of the abiotic reaction in the absence of template (sample 3); 5) Product of the abiotic reaction in the presence of template (sample 5); E) 64 mer oligomer DNA used as a template; F) Height of particles obtained for a 50 base ssDNA measured by Hansma and Laney (1996 supra).

Example XX

Is a Restriction Site Present in the dsDNA Product?

In order to further assess the transfer of a sequence from the template to a replicated DNA strand, the product of the complete reaction mixture (sample 5) was digested with FauI restriction enzyme as described above. If the reaction produced a $GGCG(N)_6$ sequence complementary to the $CCGC(N)_4$ present in the template, it would form a restriction site for the FauI endonuclease. The digestion reduced the intensity of the fluorescent bands observed in the acrylamide gel (FIG. 14A) and products of smaller size became apparent in the intensity profile of the digested product (FIG. 14B).

Figure 14:
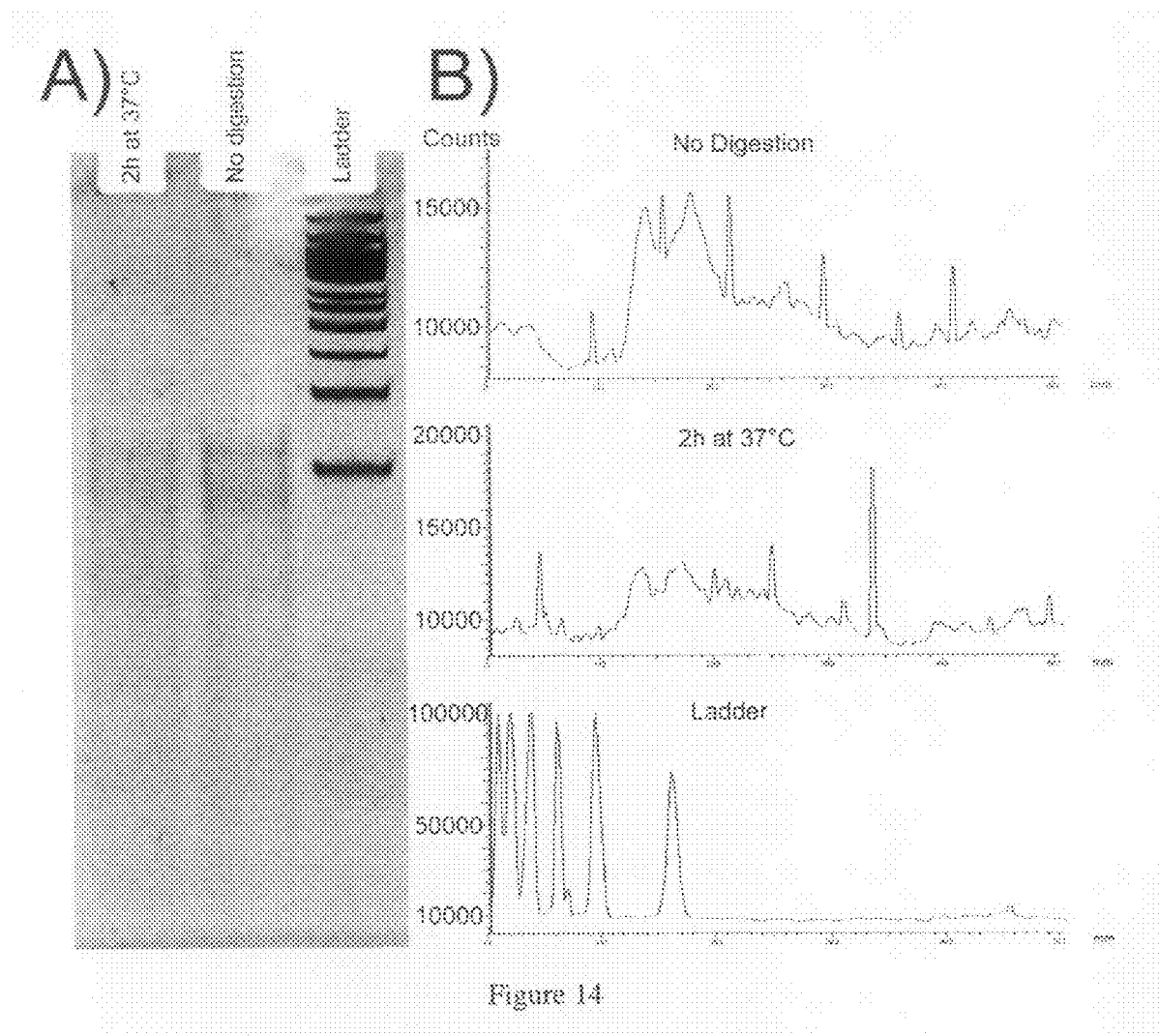
FIG. 14 illustrates an exemplary restriction enzyme assay.

FIG. 14 illustrates a restriction enzyme assay. A) Gel electrophoresis image of the abiotic reaction product before and after the digestion with FauI restriction enzyme. The gel preparation was as for FIG. 14, but twice the amount of sample was used in each lane. Lanes containing the abiotic reaction product before and after 2 h at 37° C. FauI restriction enzyme are shown.

However, the abiotic product was not completely digested. A possible explanation for this effect could be the presence of secondary structures in the replicated dsDNA product, such as those illustrated in FIG. 15a-c. These structures could perturb the binding of the enzyme to the substrate and lead to a partial digestion. Although this assay does not prove that the whole sequence is replicated with 100% fidelity, it shows that there is some double stranded DNA present in the system, which can be cleaved by the FauI restriction enzyme. This evidence suggests that this DNA does contain at least a segment with a specifically replicated sequence.

Figure 15:
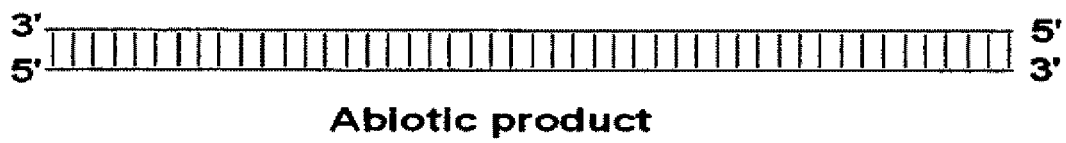
FIG. 15 illustrates product pairing possibilities.
Figure 15:
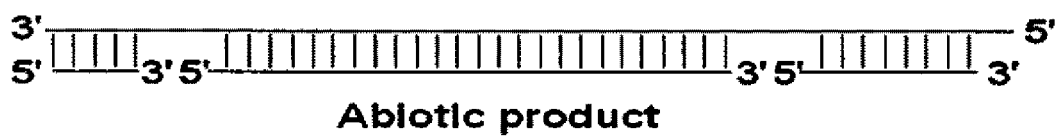
Figure 15:
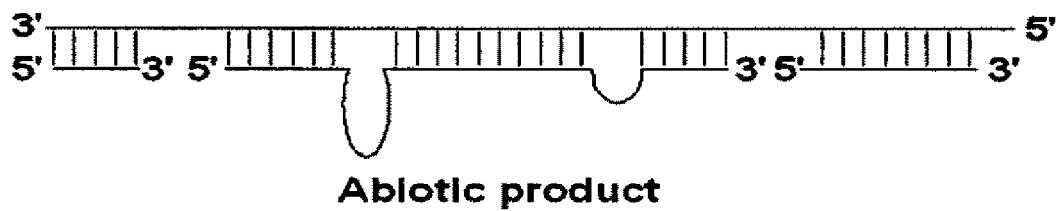

FIG. 15 illustrates product pairing possibilities. a) The product of the reaction extends completely to the full length of the template. b) The multiple sized products of the abiotic reaction pair flat at different locations of the template covering most of its length. c) The products of the abiotic reaction pair forming some structure at different locations of the template covering most of its length. The evidence presented in this work suggests that c) is the most plausible product. These results further confirmed that the method resulted in an ordering microenvironment.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

4. The method of claim 1 wherein $[H^+]$ is between $10^{-2}$ M and $10^{-8}$ M.

5. The method of claim 1 wherein the mole ratio of monomer to phospholipid is between 1:1 and 100:1.

6. The method of claim 1 wherein the phospholipid is selected from the group consisting of palmitoyl-oleoylphosphatidylcholine (POPC), palmitoyl-oleoylphosphatidic acid (POPA), lysophosphatidylcholine (LPC), phosphatidylcholine (PC), phosphatidylglycerol (PG), phosphatidylinositol (PI), phosphatidylethanolamine (PE), phosphatidylserine (PS), and sphingomyelin (SM).

7. The method of claim 1 wherein the monomer is selected from the group consisting of adenosine 5'-monophosphate, uridine 5'-monophosphate, cytosine 5'-monophosphate, guanosine 5'-monophosphate, deoxyadenosine 5'-monophosphate, deoxycytosine 5'-monophosphate, deoxyguanosine 5'-monophosphate, and thymidine monophosphate.

8. The method of claim 7 wherein the chemical bond is a phosphodiester bond between at least two mononucleotides, the method thereby synthesizing a polynucleotide.

We claim:

1. A method for synthesizing a polymer using non-enzymatic catalysis, the method comprising: (i) providing an aqueous solution of phospholipid and monomer; (ii) subjecting the aqueous solution to fluctuating temperature; (iii) subjecting the aqueous solution to fluctuating cycles of drying and hydrating; (iv) subjecting the aqueous solution to fluctuating $[H^+]$; (v) forming a chemical bond between at least two monomers thereby synthesizing a polymer using non-enzymatic catalysis, further comprising a step of adding a cofactor to the aqueous solution.

2. The method of claim 1 wherein the aqueous solution comprises from between 5% v/v water and 99% v/v water.

3. The method of claim 1 wherein the temperature is between 20° C. and 100° C.

9. The method of claim 1, wherein the cofactor is selected from the group consisting of $Mg^{2+}$, $Mn^{2+}$, $Ca^{2+}$, ATP, $NAD^+$, and $NADP^+$.

10. The method of claim 1 wherein, following step (iii), the phospholipids comprise lipid multilayers.

11. The method of claim 10, further comprising the lipid multilayers imparting an ordering microenvironment wherein the ordering microenvironment fuels the non-enzymatic catalysis of monomers to synthesize the polymer.

12. The method of claim 1 wherein the aqueous solution further comprises a template.

13. The method of claim 12 wherein the template is selected from the group consisting of a single-stranded polynucleotide, an oligopeptide, and an oligosaccharide.

14. A method for synthesizing a polymer using non-enzymatic catalysis, the method comprising: (i) providing an aqueous solution of a template, phospholipid, and non-activated substrate; (ii) subjecting the aqueous solution to fluctuating temperature; (iii) subjecting the aqueous solution to fluctuating cycles of drying and hydrating; (iv) subjecting the aqueous solution to fluctuating [$H^+$]; (v) forming a chemical bond between the template and at least one non-activated substrate; (vi) forming a chemical bond between the bonded template and non-activated substrate and at least one more non-activated substrate thereby synthesizing a polymer using non-enzymatic catalysis.

15. The method of claim 14 wherein the template is selected from the group comprising a single-stranded polynucleotide, an oligopeptide, and an oligosaccharide.

16. The method of claim 15 wherein the non-activated substrate is selected from the group consisting of adenosine 5'-monophosphate, uridine 5'-monophosphate, cytosine 5'-monophosphate, guanosine 5'-monophosphate, deoxyadenosine 5'-monophosphate, deoxycytosine 5'-monophosphate, deoxyguanosine 5'-monophosphate, and thymidine monophosphate.

17. A method for replicating a polymer template using non-enzymatic catalysis, the method comprising: (i) providing a polymer template; (ii) providing an aqueous solution of phospholipid, monomer, and a cofactor, the aqueous solution in fluid communication with the polymer template; (iii) subjecting the aqueous solution to fluctuating temperature; (iv) subjecting the aqueous solution to fluctuating cycles of drying and hydrating; (v) subjecting the aqueous solution to fluctuating [$H^+$]; (vi) forming a chemical bond between at least two monomers, the two monomers corresponding to a portion of the polymer template, thereby replicating a polymer template using non-enzymatic catalysis.

18. The method of claim 17 wherein the template is selected from the group comprising a single-stranded polynucleotide, an oligopeptide, and an oligosaccharide.

19. The method of claim 18, wherein the monomer is selected from the group consisting of adenosine 5'-monophosphate, uridine 5'-monophosphate, cytosine 5'-monophosphate, guanosine 5'-monophosphate, deoxyadenosine 5'-monophosphate, deoxycytosine 5'-monophosphate, deoxyguanosine 5'-monophosphate, and thymidine monophosphate.

20. A method for amplifying a polymer template using non-enzymatic catalysis, the method comprising: (i) providing a polymer template; (ii) providing an aqueous solution of phospholipid, monomer, and a cofactor, the aqueous solution in fluid communication with the polymer template; (iii) subjecting the aqueous solution to fluctuating temperature; (iv) subjecting the aqueous solution to fluctuating cycles of drying and hydrating; (v) subjecting the aqueous solution to fluctuating [$H^+$]; (vi) forming a chemical bond between at least two monomers, the two monomers corresponding to a portion of the polymer template; (vii) repeating steps (iii) through (vi) thereby amplifying a polymer template using non-enzymatic catalysis.

21. The method of claim 20 wherein the template is selected from the group comprising a single-stranded polynucleotide, an oligopeptide, and an oligosaccharide.

22. The method of claim 21, wherein the monomer is selected from the group consisting of adenosine 5'-monophosphate, uridine 5'-monophosphate, cytosine 5'-monophosphate, guanosine 5'-monophosphate, deoxyadenosine 5'-monophosphate, deoxycytosine 5'-monophosphate, deoxyguanosine 5'-monophosphate, and thymidine monophosphate.

23. The method of claim 5 wherein the mole ratio of monomer to phospholipid is selected from the group consisting of 1:1, 2:1, 3:1, 4:1, 5:1, 6:1, 7:1, 8:1, 9:1, 10:1, 15:1, 20:1, 25:1, 30:1, 40:1, 50:1, and 100:1.

24. The method of claim 1 wherein the monomer is an amino acid selected from the group consisting of alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine.

25. The method of claim 24 wherein the chemical bond is a peptide bond between at least two amino acids, the method thereby synthesizing a polypeptide.

\* \* \* \* \*

```
                          SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<223> OTHER INFORMATION: KDEL C-terminal tetrapeptide

<400> SEQUENCE: 1

Lys Asp Glu Leu
1

<210> SEQ ID NO 2
<211> LENGTH: 64
<212> TYPE: DNA
<213> ORGANISM: Artificial Sequence
<220> FEATURE:
<223> OTHER INFORMATION: Synthetic Construct
<220> FEATURE:
<223> OTHER INFORMATION: 64 mer DNA Template; minimal secondary
      structure

<400> SEQUENCE: 2 cccccgcct cctccgccac caccgcctcc tcctcctccg cctcctccgc caaaaaaaaa      60
aaaa                                                                 64
```